(12) United States Patent
Beyerlein et al.

(10) Patent No.: US 8,435,279 B2
(45) Date of Patent: May 7, 2013

(54) DELIVERY SYSTEM FOR A DEVICE SUCH AS A STENT

(75) Inventors: Dagmar Beyerlein, San Francisco, CA (US); Christopher Feezor, San Jose, CA (US); Karim Osman, Mountain View, CA (US); Denise Horrilleno Burns, Sunnyvale, CA (US); Carla Rosa Pienknagura, Menlo Park, CA (US); Barbara Stamberg, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1683 days.

(21) Appl. No.: 11/152,951

(22) Filed: Jun. 14, 2005

(65) Prior Publication Data

US 2006/0282152 A1 Dec. 14, 2006

(51) Int. Cl.
*A61F 2/06* (2006.01)

(52) U.S. Cl.
USPC .......................................... 623/1.11; 623/1.12

(58) Field of Classification Search .................. 623/1.11, 623/1.12
See application file for complete search history.

(56) References Cited

U.S. PATENT DOCUMENTS

| | | | |
|---|---|---|---|
| 4,580,568 A | 4/1986 | Gianturco | |
| 4,655,772 A | 4/1987 | De Liotta et al. | |
| 4,681,110 A | 7/1987 | Wiktor | |
| 4,732,152 A * | 3/1988 | Wallsten et al. | 623/1.11 |
| 4,739,762 A | 4/1988 | Palmaz | |
| 4,830,003 A | 5/1989 | Wolff et al. | |
| 4,875,480 A * | 10/1989 | Imbert | 606/194 |
| 5,026,377 A | 6/1991 | Burton et al. | |
| 5,035,706 A | 7/1991 | Gianturco et al. | |
| 5,074,845 A | 12/1991 | Miraki et al. | |
| 5,391,172 A | 2/1995 | Williams et al. | |
| 5,421,955 A | 6/1995 | Lau et al. | |
| 5,445,646 A * | 8/1995 | Euteneuer et al. | 606/198 |
| 5,514,154 A | 5/1996 | Lau et al. | |
| 5,534,007 A * | 7/1996 | St. Germain et al. | 623/1.11 |
| 5,569,295 A | 10/1996 | Lam | |
| 5,571,135 A * | 11/1996 | Fraser et al. | 623/1.12 |
| 5,603,721 A | 2/1997 | Lau et al. | |

(Continued)

FOREIGN PATENT DOCUMENTS

| | | |
|---|---|---|
| WO | WO 94/15549 | 7/1994 |
| WO | WO 95/11055 A | 4/1995 |

(Continued)

OTHER PUBLICATIONS

PCT Invitation to Pay Additional Fees for PCT Appln No. US2006/020073, mailed Dec. 1, 2006 (6 pages).

(Continued)

*Primary Examiner* — Gregory Anderson
(74) *Attorney, Agent, or Firm* — Angela M. Augustin; Blakely Sokoloff Taylor & Zafman LLP

(57) ABSTRACT

A delivery system for a medical device. The delivery system comprises an inner member, a retractable sheath disposed over the inner member and being slideable over the inner member, and a retraction member coupled to the retractable sheath and disposed at least in portion within the retractable sheath, the retraction member being slideable over the inner member. An axial movement of the retraction member retracts or actuates the retractable member.

4 Claims, 12 Drawing Sheets

U.S. PATENT DOCUMENTS

| | | | |
|---|---|---|---|
| 5,662,703 A * | 9/1997 | Yurek et al. | 623/1.12 |
| 5,817,101 A * | 10/1998 | Fiedler | 623/1.11 |
| 5,935,135 A | 8/1999 | Bramfitt et al. | |
| 6,059,813 A * | 5/2000 | Vrba et al. | 606/198 |
| 6,113,608 A * | 9/2000 | Monroe et al. | 623/1.11 |
| 6,254,611 B1 * | 7/2001 | Vrba | 606/108 |
| 6,605,109 B2 | 8/2003 | Fiedler | |
| 6,673,101 B1 | 1/2004 | Fitzgerald et al. | |
| 6,702,843 B1 | 3/2004 | Brown et al. | |
| 6,709,454 B1 | 3/2004 | Cox et al. | |
| 6,824,545 B2 | 11/2004 | Sepetka et al. | |
| 6,942,682 B2 | 9/2005 | Vrba et al. | |
| 2001/0012959 A1 | 8/2001 | Blaeser et al. | |
| 2002/0058951 A1 | 5/2002 | Fiedler | |
| 2002/0077592 A1 | 6/2002 | Barry | |
| 2003/0114915 A1 | 6/2003 | Mareiro et al. | |
| 2004/0158307 A1 | 8/2004 | Jones et al. | |
| 2004/0158315 A1 | 8/2004 | Cox et al. | |
| 2005/0090887 A1 | 4/2005 | Pryor | |
| 2005/0228438 A1 | 10/2005 | Sachar et al. | |
| 2006/0030923 A1 | 2/2006 | Gunderson | |

FOREIGN PATENT DOCUMENTS

| | | |
|---|---|---|
| WO | WO 95/23008 A1 | 8/1995 |
| WO | WO 98/57692 A1 | 12/1998 |
| WO | WO 99/47075 A1 | 9/1999 |
| WO | WO 00/78249 A1 | 12/2000 |
| WO | WO 02/38084 A2 | 5/2002 |
| WO | WO 2004/098462 A1 | 11/2004 |

OTHER PUBLICATIONS

PCT International Preliminary Report on Patentability and Written Opinion for PCT/US2006/020073, mailed Jan. 3, 2008, 11 pages.
PCT International Search Report and Written Opinion for PCT Appln No. US2006/020073, mailed on Jan. 3, 2007 (20 pages).

* cited by examiner

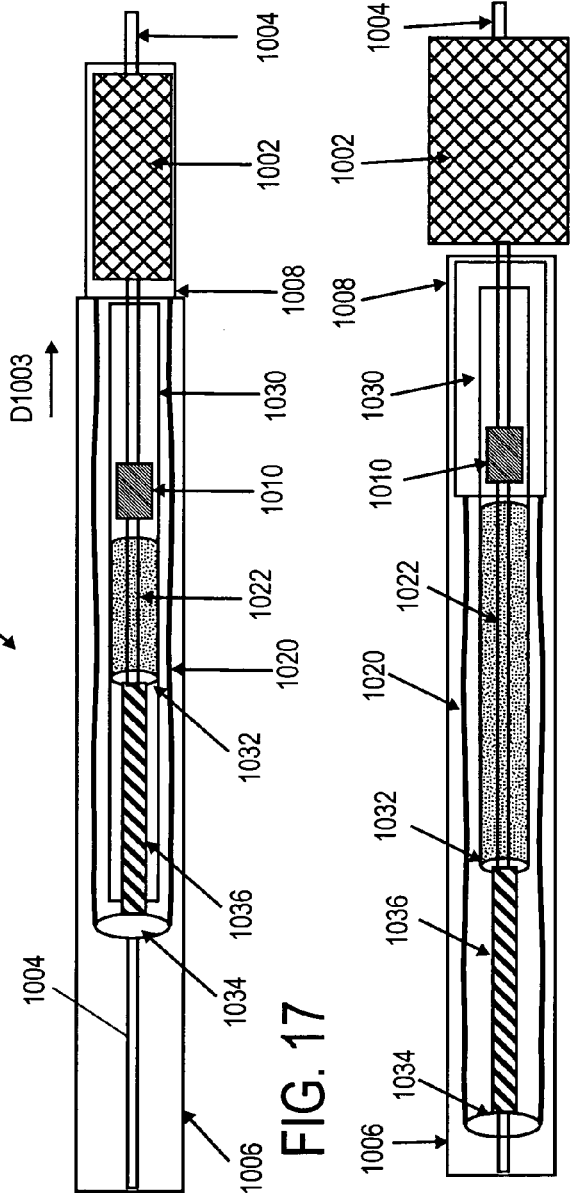
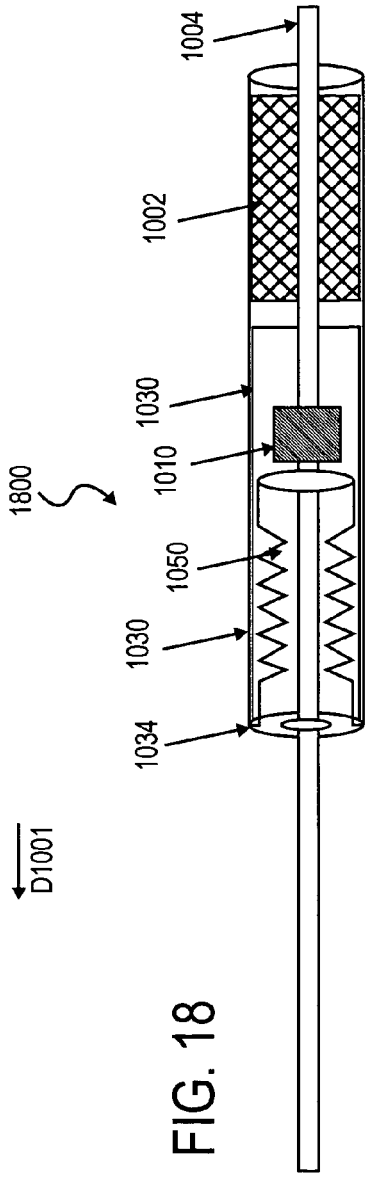
FIG. 16
FIG. 17
FIG. 18

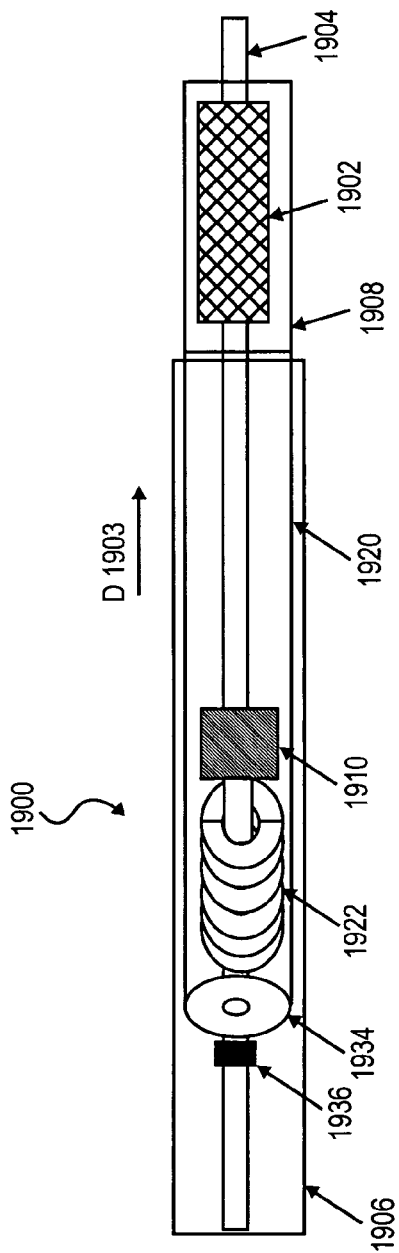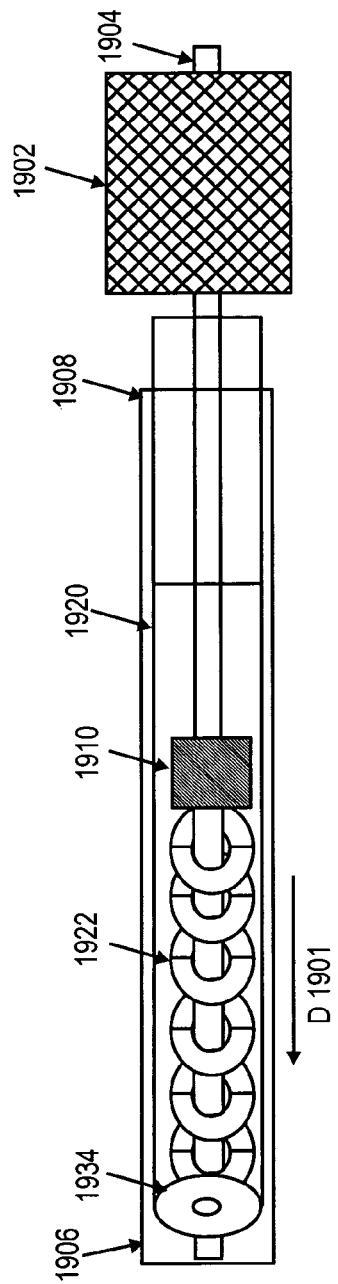
FIG. 19
FIG. 20

DELIVERY SYSTEM FOR A DEVICE SUCH AS A STENT

BACKGROUND

1. Field

The present invention pertains to a medical device delivery catheter system. A delivery catheter system is typically used to deliver devices such as stents, stent-grafts, grafts, or other diagnostic or therapeutic devices.

2. Discussion of Related Art

It is desirable in various situations to access a vessel, a constricted vessel portion for purposes such as maintaining an open passageway through a vessel portion. Such situations arise, for example, in conjunction with arteriosclerosis that restricts or stops blood flow through a vessel. In many procedures, a guiding catheter is percutaneously introduced into a patient's vessel. For instance, a guide catheter is introduced into the patient's cardiovascular system into a coronary artery in a typical percutaneous transluminal coronary angioplasty procedure. Often, a guidewire is used in conjunction with fluoroscopy to advance the catheter into the vessel. Procedures that utilize such a guide catheter include opening an artery, preventing arterial closure, and implanting a prosthesis, stent, stent-graft, graft, or other device to maintain vascular patency. In many procedures, a guide catheter helps delivering the particular device (e.g., a stent) to a treatment site and needs to be withdrawn after the device is delivered. Moreover, in certain applications, the guide catheter also functions as a delivery catheter or a housing for a delivery catheter for the device. Withdrawing the guide catheter or the delivery catheter is often a challenging task as illustrated in FIGS. 1-3.

To help prevent arterial closure, repair dissection, or prevent restenosis following dilatation, a physician can implant an intravascular prosthesis, or a stent or other device such as a stent-graft, or a graft, for maintaining vascular patency inside the artery at the lesion. There are typically two types of stents, a self-expanding stent and a balloon expandable stent. The balloon expandable stent is delivered on a balloon and the balloon is used to expand the stent. The self-expanding stent may be made of shape memory materials such as Nitinol (NiTi) or constructed of regular metals but of a configuration that allows self-expansion. The stents can also be made of polymeric materials.

Stents are generally tubular-shaped devices which function to hold open a segment of a blood vessel or other anatomical lumen. Stents have been used for many treatment procedures. For instance, stents have been used to maintain vascular patency, open up an obstructed artery, repair aneurysms, repair dissections, support artificial vessels, and support other lumens in a patient's body.

FIG. 1 illustrates an example of a conventional catheter delivery system 100 for a self-expanding stent. In one example, a stent 102 is placed within a retractable sheath 108 in a compressed, collapsed, or undeployed state. The stent 102 is placed between an inner member 104 and the sheath 108, which could be a catheter. If there is a balloon to deploy the stent 102 (if the stent 102 is not self-expandable), the balloon (not shown) is placed under the stent 102 and outside the inner member 104. The inner member 104 may be configured to accept a guidewire 112 to help maneuver the stent delivery system 100 to a treatment site. The stent 102 and the inner member 104 are placed within an outer member 106. In conventional delivery methods, to deliver the stent 102, the retractable sheath 108 is pulled back proximally to expose the stent 102 and to allow the stent 102 to deploy as shown in FIG. 2 while the inner member 104 remains in place. In some cases, the sheath 108 is bonded to the outer member 106 and withdrawing the outer member 106 also retracts the sheath 108 to deploy the stent 102. In another example, a pullback wire (not shown) is included. The pullback wire is attached to the sheath 108 such that one can pull on the pullback wire to independently withdraw the sheath 108 in order to deploy the stent 102. A handle (not shown) with a pullback mechanism is provided at the proximal end of the delivery catheter system 100 to retract the sheath 108. In one example, a stopper 110 is provided to prevent the stent 102 from sliding proximally while the sheath 108 is being withdrawn. After the stent 102 is deployed, the catheter assembly is removed.

Delivery systems such as those described work well in relatively simple vascular anatomies. However, such systems do not always provide a smooth withdrawal of the sheath 108 in a situation where the delivery systems have to go through tortuous pathways, such as those seen in the anatomy of the coronary arteries. The tortuous pathways often cause buckling or kinking of the inner member 104, outer member and catheter assembly during sheath retraction and increase contact areas 120 as well as frictional forces between the fixed inner member 104 and the sliding outer member 106 and the sheath 108 as illustrated in FIG. 3. For instance, the inner member 104 starts to lock on the outer member 106 due to crimping, kinking, friction, or buckling of the inner member 104 that is caused by a tortuous pathway. Thus, during an interventional process, it may be difficult to withdraw the sheath 108 or other components of the delivery system and in extreme cases, the stent 102 may be undesirably moved or withdrawn. Some delivery systems also provide a separate lumen for a pullback wire that is used to retract the sheath 108. These delivery systems suffer the same problem caused by the buckling or kinking of the delivery systems due to the tortuous pathways. The forces between the fixed inner member 104 and the sliding outer member 106 and/or the sheath 108 can become so large that the delivery system locks and prevents sheath retraction and potentially, stent deployment.

In some cases, to prevent the buckling problem, the inner member 104 needs to be stiff to prevent buckling or kinking during the sheath retraction process. However, having a stiff component in the delivery system is not desirable especially when the delivery system needs to go through tortuous pathways. Furthermore, with a requirement that all the components in a delivery system be as small in dimension as possible for various vasculature pathways, the outer member 106 and the inner member 104 have very similar diameter dimensions making the buckling or kinking problem even more pronounced. Accordingly, there is a need for a system that accomplishes the delivery of a medical device within vasculature while addressing the shortcomings found in conventional devices. The present invention satisfies these and other needs.

SUMMARY

Briefly and in general terms, the present invention is directed toward a system that accomplishes the advancement and delivery of a medial device within vasculature. In one particular aspect, embodiments of the present invention pertain to a stent and/or a stent delivery system that can deploy the stent and withdraw the delivery system.

One embodiment pertains to a device that comprises an outer member, an inner member disposed within the outer member, a sheath disposed over the inner member, and a flexible intermediary member extending between the sheath and the outer member and foldable within the outer member.

The sheath is slideable over the inner member. A seal is created between the flexible intermediary member and the outer member. The flexible intermediary member is slideable over the inner member. The sheath is retracted when a negative pressure is created so as to cause the flexible intermediary member to fold within the outer member to retract the sheath.

In another embodiment, the present invention pertains to a device that comprises an outer member, an inner member disposed within the outer member, a sheath disposed over the inner member, and a compressible member connected to the sheath at least at one point and is slideably disposed on the inner member. The sheath is slideable over the inner member. The compressible member is axially expandable. The sheath is retracted when the compressible member is axially expanded.

In a further embodiment, the present invention pertains to a device that comprises an outer member, an inner member disposed within the outer member, a sheath disposed over the inner member, and a compressible member connected to the sheath at least at one point and is slideably disposed on the inner member. The sheath being slideable over the inner member. The compressible member is expanded in a delivery state. The sheath is retracted when the compressible member is axially compressed.

In yet a further embodiment, the invention pertains to a device that comprises an outer member, an inner member disposed within the outer member, a sheath disposed over the inner member, and a compressible member connected to the sheath and slideably disposed on the inner member. The sheath is slideable over the inner member. The compressible member is expandable. A constraint member is further disposed outside the compressible member. The constraint member defines an axial expanding limit for the compressible member. The sheath is retracted when the compressible member is expanded.

Another particular embodiment relates to a device that comprises an outer member, an inner member disposed within the outer member, a sheath disposed over the inner member, and a compressible spring member connected to the sheath and slideably disposed on the inner member. The sheath is slideable over the inner member. The compressible spring member is axially expandable. The sheath is retracted when the compressible spring member is axially expanded.

In yet another particular embodiment, the invention relates to a device that comprises an outer member, a delivery member disposed within the outer member, and an expandable member configured to have prongs when in a non-fully inflated state and to have no prongs when fully inflated, the prongs of the expandable member being configured to hold a medical device in a non-deployed state when the expandable member is in the non-fully inflated state, and the expandable member being coupled to the delivery member.

Other embodiments of the present invention pertain to methods of delivering a device to a vessel or a treatment site using the exemplary delivery systems in accordance with the present invention. Other features and advantages of the present invention will become apparent from the following detailed description, taken in conjunction with the accompanying drawings, which illustrate, by way of example, the principles of the invention.

BRIEF DESCRIPTION OF THE DRAWINGS

The present invention is illustrated by way of example and not limitation in the figures of the accompanying drawings, in which like references indicate similar elements and in which:

FIGS. 16-18 illustrate other exemplary embodiments of a delivery system of the present invention that employs an expandable member to withdraw a sheath;

FIGS. 19-20 illustrate an exemplary embodiment of a delivery system of the present invention that employs a spring system to withdraw a sheath;

DETAILED DESCRIPTION

The exemplary embodiments of the present invention pertain to delivery systems for medical devices such as a stent.

In the following description, for purposes of explanation, numerous specific details are set forth in order to provide a thorough understanding of the present invention. It will be evident, however, to one skilled in the art, that the present invention may be practiced without these specific details. In other instances, specific apparatus structures and methods have not been described so as not to obscure the present invention. The following description and drawings are illustrative of the invention and are not to be construed as limiting the invention.

Exemplary embodiments of the present invention pertain to a catheter assembly that can be used to deliver a medical device such as a stent. Although the embodiments of the present invention refer to a stent as the medical device, it is to be understood that the embodiments of the present invention can be used with other medical device. As will be discussed below in more detail, an exemplary catheter system of the present invention includes an inner member, a retractable sheath slidably disposed over the inner member, and a retraction member coupled to the retractable sheath and disposed, at least in portion, within the retractable sheath. When the retraction member is moved axially, the retraction member according causes the retractable sheath to retract. The catheter system can also include an outer member to house the inner member, the retractable sheath, and the retraction member for delivery into a vessel. The catheter system can be used to deliver a medical device to the vessel. In one embodiment, the medical device is disposed on the outer surface of the inner member and supported by the inner member, and confined by the retractable sheath during delivery. To deploy the medical device, the retraction member is moved and the retractable sheath is retracted to unconfine or expose the medical device thus deploying the medical device.

Figure 1:
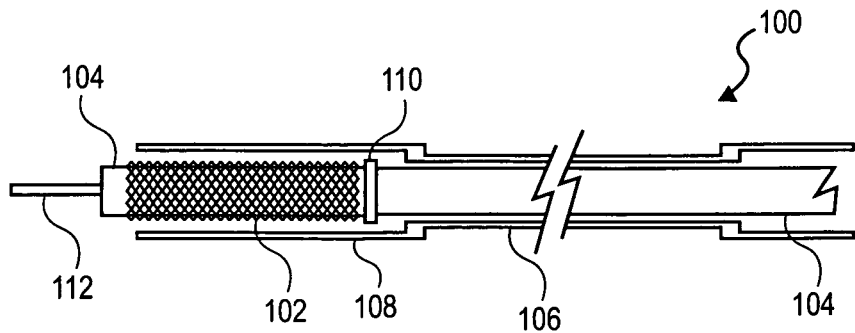
FIGS. 1-2 illustrate an exemplary conventional delivery system for a stent.
Figure 2:
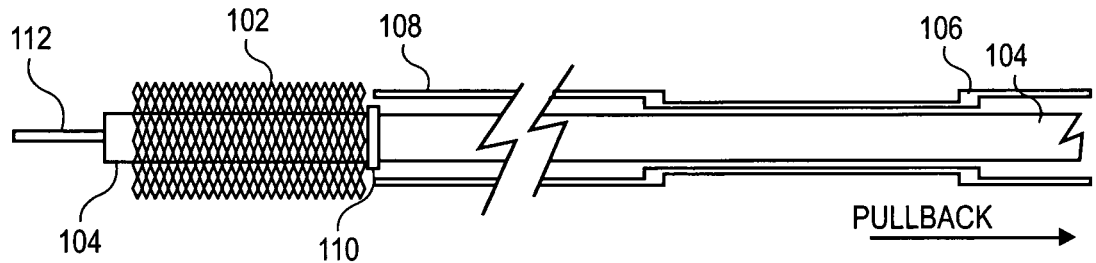
Figure 3:
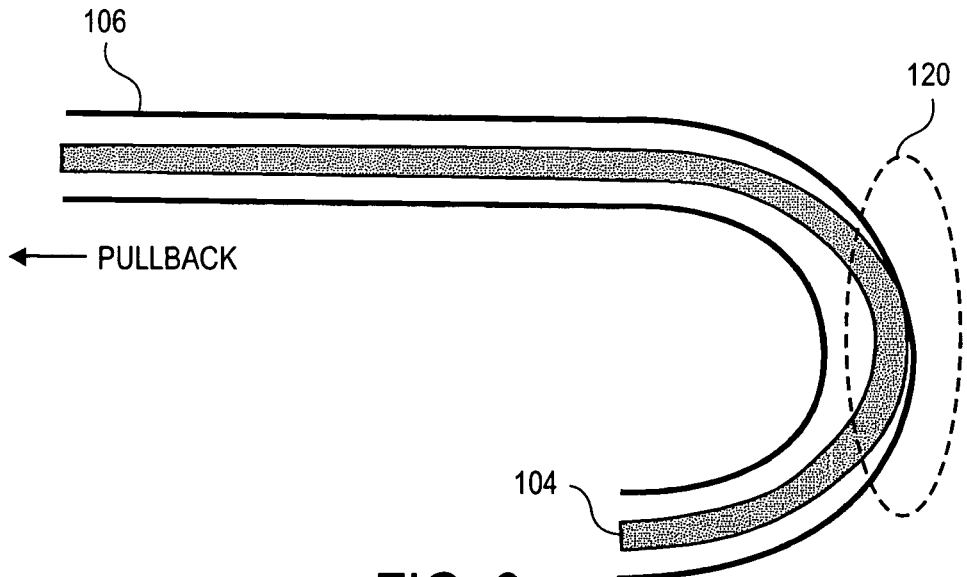
FIG. 3 illustrates a potential interference problem observed in a conventional delivery system when the delivery system has to go through a tortuous pathway.
Figure 4:
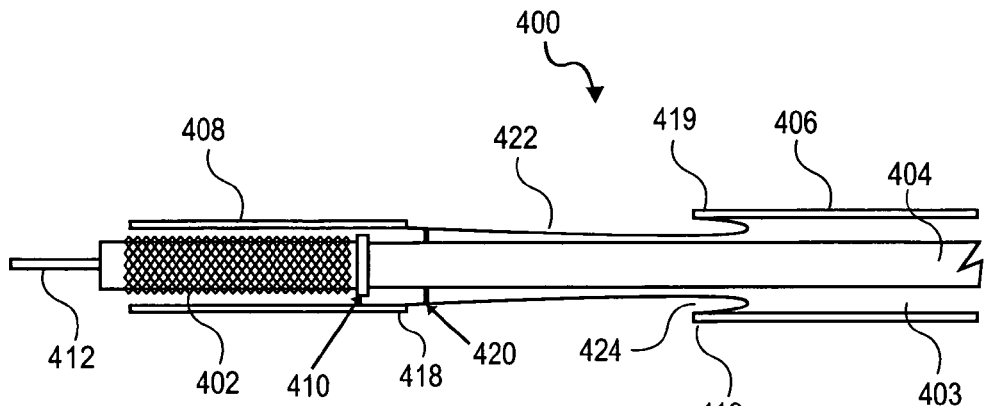
FIGS. 4-6 illustrate an exemplary embodiment of a delivery system of the present invention that employs a flexible member to withdraw a sheath.
Figure 5:
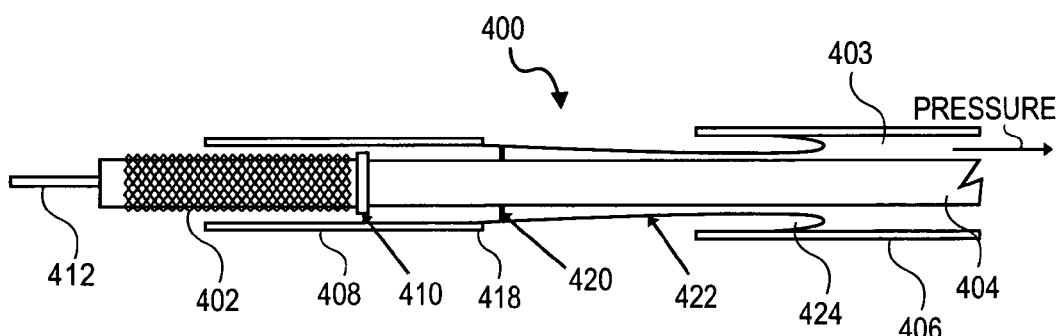
Figure 6:
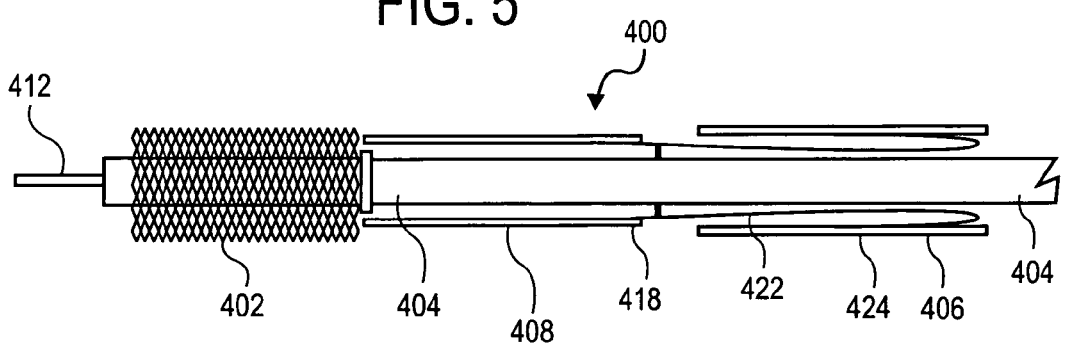

FIGS. 4-6 illustrate an exemplary embodiment of a delivery system 400 that can deliver a medical device in a tortuous pathway. The delivery system 400 utilizes a pneumatic sheath retraction mechanism to address problems associated with buckling or kinking of members or components of a delivery catheter system associated with pullback mechanisms that extend the entire length of the catheter. The present embodiment implements a pneumatic pullback through the introduction of a thin and very flexible intermediary member bonded between a retractable sheath and an outer member of the delivery system 400.

In one embodiment, the delivery system 400 comprises an outer member 406, an inner member 404, a retractable sheath 408, and a flexible intermediary member 422. The flexible intermediary member 422 is the retraction member previously mentioned. The inner member 404 is disposed within the outer member 406. The retractable sheath 408 is disposed over and extends over at least a portion of the inner member 404. The flexible intermediary member 422 mechanically bonds the retractable sheath 408 to the outer member 406. The flexible intermediary member 422 may be made of a soft and flexible material such as Latex or other conventional polymers.

In one embodiment, the inner member 404 and the outer member 406 are flexible tubes with lumens extending there through. Thus, the inner member 404 is disposed within a lumen of the outer member 406. The retractable sheath 408 may also have a configuration of a tube and is placed on the outside of the inner member 404 and within the outer member. The retractable sheath 408 can thus ride between the inner member 404 and the outer member 406. Alternatively, in one embodiment, the retractable sheath 408 is configured to slide over the outer member 406.

The retractable sheath 408 is configured so that the retractable sheath is slideable over the inner member 404. In one embodiment, the flexible intermediary member 422 is foldable within the outer member 406. A portion of the flexible intermediary member 422 is also disposed within the retractable sheath 408. In one embodiment, the flexible intermediary member 422 is folded over or within itself and is bonded to the outer member 406 with a fold 424 tucked inside the outer member 406. A seal is provided or created between the flexible intermediary member 422 and the outer member 406. In one embodiment, a distal portion of the flexible intermediary member 422 is attached to the retractable sheath 408 at junction 418 and a proximal portion of the flexible intermediary member 422 is attached to the outer member 406 at junction 419. Additionally, a sealing member 420 is provided between the inner surface of the flexible intermediary member 422 and the outer surface of the inner member 404. The sealing member 420 is slideable on the outer surface of the inner member 420 and could be a bearing to facilitate such sliding. The sealing member 420 enables the flexible intermediary member 422 to slide over the inner member 404 while still providing a good seal with the inner member 404. In one embodiment, the sealing member 420 is a bearing that is coupled to a distal portion of the intermediary member 422 and rests or engages the outer surface of the inner member 404 but is slideable across the outer surface of the inner member 404. In another embodiment, the sealing member 420 is an O-ring that is coupled to a distal portion of the intermediary member 422 and made to be slideable across the outer surface of the inner member 404. A seal is created between the outer member 406 and the flexible intermediary member 422. The flexible intermediary member 422 is slideable over the inner member 404 while folding over on itself and into the outer member 406. A space 403 is provided between the inner member 404 and the outer member 406 and the between the inner member 404 and the flexible intermediary member 422.

The retracting of the retractable sheath 408 is initiated by drawing a negative pressure in the space 403. As the negative pressure is created, the flexible intermediary member 422 folds onto itself and folds into the outer member 406 as shown in FIGS. 5-6. The fold section 424 becomes larger and larger as the negative pressure is applied to the space 403. The negative pressure essentially sucks the flexible intermediary member 422 into the outer member 406 thus retracting the sheath 408. The flexible intermediary member 422, in one embodiment, is not stretchable so that when the negative pressure is applied, the flexible intermediary member 422 can fold into the outer member 406 to cause the retractable sheath 408 to retract. It is to be understood that in some embodiments, the pressure can be applied in a way that causes the flexible intermediary member 422 to unfold thus actuating the sheath 408 in an opposite direction of the sheath 408 retraction, e.g., applying a positive pressure. The capability of the sealing member 422 to create an adequate seal while allowing the flexible intermediary member 422 to be slideable over the inner member 404 may also be enhanced with an application of a viscous and/or biocompatible lubricant between the inner member 404 and the flexible intermediary member 422. In one embodiment, a lubricious or slippery coating is applied over the inner member 404 to facilitate the sliding of the sealing member 422 on the outer surface of the inner member 404.

The flexible intermediary member 422 allows the delivery system 400 to be bent (as the system 400 goes through tortuous pathway) without causing problems with sheath 408 retraction.

A proximal adapter (not shown) is connected to the proximal end of the delivery system 400. The proximal adapter is configured to facilitate applying a negative pressure into the space 403. The proximal adapter is coupled to the end of the catheter system (e.g., the outer member 406) of the delivery system 400, in one embodiment. Many devices known in the art can be coupled to a catheter system (e.g., to the outer member 406) to create a negative pressure in the system 400 such as a syringe or vacuum pump system. In the present embodiment, to create the negative pressure, the syringe is pulled back to draw air out of the space 403 to create a negative pressure that causes the flexible intermediary member 422 to fold into itself and fold into the inner space of the outer member 406. This action will then cause the retractable sheath 408, which is attached to the flexible intermediary member 422 to retract proximally.

In one embodiment, the inner member 404 includes a lumen that can accommodate a guidewire 412. The guidewire 412 helps maneuvering the delivery system 400 to the treatment site.

Moreover, a medical device can be included in the delivery system 400. The medical device is supported by the inner member 404 and is covered, confined, contained, constrained, or constricted by the retractable sheath 408 during delivery. When the retractable sheath 408 is retracted, the medical device is exposed or additionally, deployed. In one embodiment, the medical device is a stent 402 as known in the art. The stent 402 can be compressed or collapsed and placed on the outside or outer surface of the inner member 404 and covered or constrained by the retractable sheath 408. When the retractable sheath 408 is retracted, the stent 402 is deployed. In one aspect, the stent 402 is a self-expanding stent and as such, the retraction of the retractable sheath 408 would allow the stent 402 to return to its uncollapsed or non-compressed state and be deployed in a vessel. The stent 402 can be made of a shape memory material such as Nickel Titanium (NiTi), Nitinol, a superelastic material, or a self-expanding polymeric material. Examples of self-expanding stents can be found in U.S. Pat. Nos. 4,580,568; 4,830,003; 6,709,454; and U.S. Pub. No. 2004/0158315, which are hereby incorporated by reference.

In another embodiment, the stent 402 is deployable by a balloon and in such embodiment, a balloon (not shown) is provided underneath the stent 402. The balloon is configured to be inflated as is known by the art. Inflation of the balloon would allow the stent 402 to expand after the retractable sheath 408 is retracted or withdrawn. Examples of expandable stents can be found in U.S. Pat. Nos. 5,603,721; 5,569,295; 5,514,154; 5,421,955; 4,739,762; and 4,655,772, which are hereby incorporated by reference.

In one particular embodiment, a stopper 410 is provided on the outer surface of the inner member 404. The stopper 410 can be affixed to the outer surface of the inner member 404. The stopper 410 prevents the compressed stent 402 from sliding proximally on the inner member during the delivery process or during sheath 408 retraction. The stopper 410 can be an O-ring, an annular collar, or a fixture placed on the outer surface of the inner member 404. The stopper 410 is placed proximally or inferior to the proximal end of the stent 402. When the stent 402 is in its compressed, collapsed, or undeployed state, the stopper 410 is slightly bigger than the stent 402 to prevent the stent 402 from sliding in the proximal direction. When the stent 402 is fully deployed, the stent 402 need not be stopped by the stopper 410. The stent 402 is deployed. After the stent 402 is deployed, such as against an inner wall of the vessel the delivery system 400 may be withdrawn and the inner member 404 is withdrawn from within the stent 402.

In one embodiment, the stent 402 is coated with an antiproliferate agent to control cell growth over the stent 402 once it is implanted into a lumen. In one embodiment, the stent 402 is deployed into a vessel such as an artery (not shown) that has what is known in the art as a vulnerable plaque section, in a manner such that the stent 402 opposes the vulnerable plaque section. After the implantation, the stent 402 promotes cell growth over the stent 402 and hence over the vulnerable plaque section or a fibrous cap of the vulnerable plaque. The cell layer acts to protect the vulnerable plaque from rupturing and possibly occluding the artery. The cell growth may need to be controlled so that uncontrolled cell growth does not occur and in turn, occlude the artery. The stent 402 can thus be coated with an antiproliferate agent that can control the cell growth over the stent 402. Examples of an antiproliferate agent include Taxol (by Bristol-Myers Squibb Company), Everolimus (by Guidant Corporation), and Sirolimus (by Cordis Corporation), or derivative thereof.

Other medical devices can also be delivered by the delivery system 400. Devices such as a mitral valve repair device, a stent-graft, a graft, a camera, a diagnostic device, or other therapeutic devices can also be configured so that each can be supported by the inner member 404 and delivered by the system 400 wherein retracting the retractable sheath 408 would allow the device to be deployed or exposed. The medical device may include its own delivery system or may be configured so that the sheath 408 can act as the delivery system for the medical device.

Figure 7A:
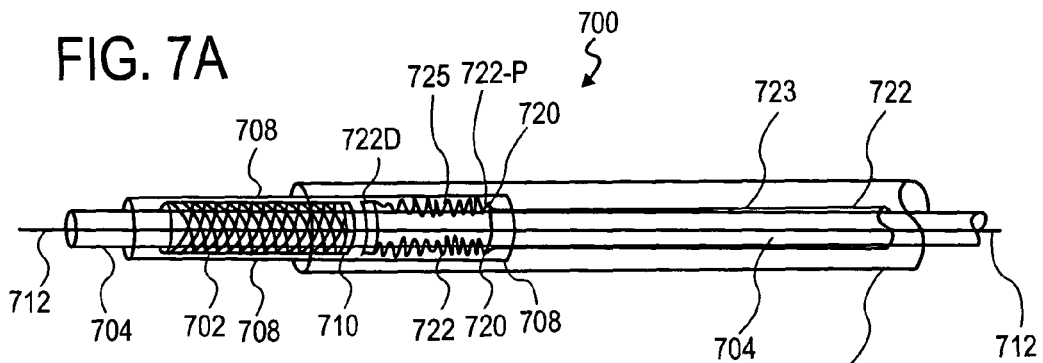
FIGS. 7A-7C illustrates an exemplary embodiment of a delivery system of the present invention that employs a compressible member to withdraw a sheath.
Figure 7B:
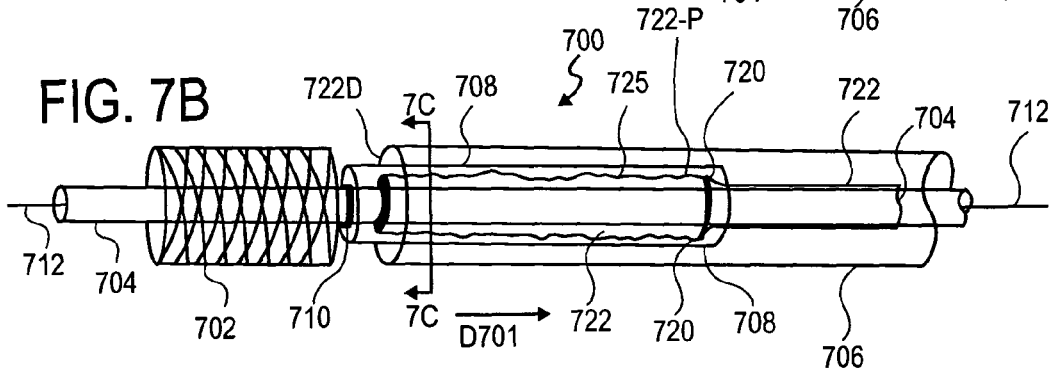
Figure 7C:
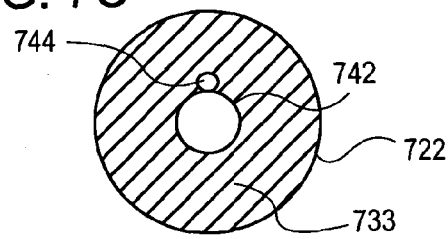

FIGS. 7A-7C illustrate another exemplary embodiment of a delivery system 700 that can deploy a medical device (e.g., a stent) in a tortuous pathway. In the present embodiment, the delivery system 700 comprises an outer member 706, an inner member 704 disposed within the outer member 706, a retractable sheath 708 disposed over the inner member 704, and a compressible member 722 mechanically connected to the sheath 708 at least at one point and is slideably disposed on outer surface of the inner member 704. The compressible member 722 is the retraction member previously mentioned. At least a portion of the compressible member 722 is disposed within the retractable sheath 708. The retractable sheath 708 is slideable over a portion or all of the inner member 704. The compressible member 722 is axially expandable and compressible. In one embodiment, the sheath 708 is retracted proximally when the compressible member 722 is axially expanded in the proximal direction ($D_{701}$).

It is to be understood that the compressible member 722 can go from initially being compressed to be axially expanded to cause the retractable sheath 708 to retract or actuate over the inner member 704. Alternatively, the compressible member 722 can go from initially being expanded to be axially compressed to cause the retractable sheath 708 to retract or actuate over the inner member 704.

The delivery system 700 employs a pullback mechanism that utilizes a compressible member 722 that can axially expand and compress to address problems associated with buckling or kinking of delivery system's components observed in conventional catheter delivery systems. The present embodiment implements the compressible member 722, which could be a bellow structure, to retract the retractable sheath 708 relative to the inner member 704 of the delivery system 700. In one embodiment, the compressible member 722 is expanded in the proximal direction of the delivery system 700 causing the retractable sheath 708 to proximally retract. FIGS. 7A-7B illustrate that the compressible member 722 begins in a delivery state with a compressed configuration (FIG. 7A). The distal portion 722-D of the compressible member 722 is adhered or mechanically fixed on the outer surface of the inner member 704. The distal portion 722-D of the compressible member 722 is fixed and is not slideable over the outer surface of the inner member 704. The compressible member 722 is expanded proximally which causes the retractable sheath 708 that is connected to the proximal portion of the compressible member 722 to be retracted proximally (FIG. 7B). A medical device (e.g., stent 702) supported by the inner member 704 and covered by the retractable sheath 708 during delivery can be exposed and/or delivered when the retractable sheath 708 is retracted.

The retractable sheath 708 is disposed over the inner member 704 and has a length that is sufficient to allow the sheath 708 to cover a medical device (e.g., a stent 702) during the delivery process. The retractable sheath 708 also couples to a portion of the compressible member 722 so that when the compressible member 722 is axially and proximally expanded, the retractable sheath 708 is proximally retracted. In one embodiment, the retractable sheath 708 is connected/fixed to the compressible member 722 at a point or points on the compressible member 722. FIGS. 7A-7B illustrate that the retractable sheath 708 connects to the compressible member 722 directly at locations 720. In one embodiment, the retractable sheath 708 extends the entire length of the compressible member 722. Since the compressible member 722 is adhered to the inner member 704 as previously mentioned, when the compressible member 722 is expanded, the compressible member 722 expands in one direction dragging with it the retractable sheath 708 in that direction. The compressible member 722 can be connected to the retractable sheath 708 through one or more wires. In another embodiment, the compressible member 722 is connected directly to the retractable sheath 708 at least at one point on the sheath 708. The compressible member 722 can be connected to the retractable sheath 708 using adhesive bonding, fusion bonding, mechanical bonding, mechanical wiring, welding, or other suitable techniques.

Figure 9:
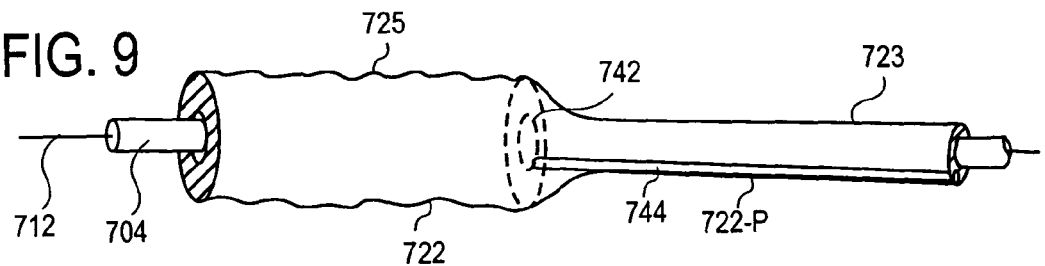

The compressible member 722 includes a distal pleated section 725 and a proximal section 723 (FIGS. 7A and 9). The proximal section 723 is essentially a tube while the distal pleated section 725 has pleats (much like that of an accordion or a bellow). When a fluid is injected into the compressible member 722, the distal pleated section 725, can expand as the pleats unfold, while the proximal section 723 does not have pleats to expand. This configuration allows the distal pleated section 725 to axially expand or expand longitudinally when fluid (e.g., air) is injected. In one embodiment, the distal pleated section 725 is disposed within the retractable sheath 708. When the compressible member is expanded, the distal pleated section 725 expands within the retractable but elongates in the proximal direction causing the retractable sheath 708 to retract proximally.

The distal pleated section 725 of the compressible member 722 allows the compressible member 722 to be compressed and expanded. Furthermore, the distal pleated section 725 also allows the delivery system 700 to be bent (as the system 700 goes through tortuous pathway) without kinking and without causing problems with sheath 708 retraction.

Figure 8:
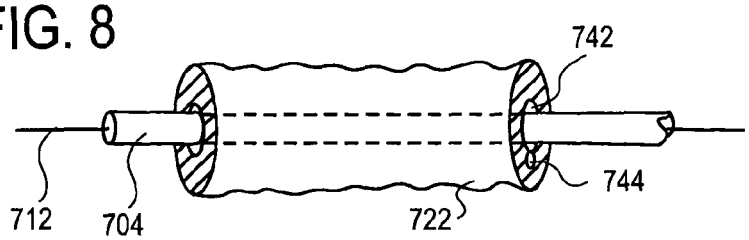
FIGS. 8-11 illustrate various exemplary embodiments of a compressible member that can be used with the delivery system shown in FIGS. 7A-7C.

In a particular aspect, the compressible member 722 includes a lumen 744 (FIG. 7C) so that the compressible member 722 can be filled with fluid via the lumen 744. FIG. 7C illustrates a cross section of the compressible member 722 at the distal pleated section 725. The compressible member 722 also includes a wall 733 as shown in this cross section. For ease of illustration, the lumens 742 and 744 are not shown in FIGS. 7A-7B but are shown in this cross section. The compressible member 722 also includes another lumen 742 that allows the compressible member 722 to be placed over the inner member 704 as shown in FIG. 8. For ease of illustration, the other components of the catheter system shown in FIGS. 7A-7B are not illustrated in FIG. 8. However, it should be understood that the compressible member 722 of the embodiment of FIG. 8 would be coupled to these other components of the catheter system as shown in FIGS. 7A-7B. In one embodiment, the lumens 742 and 744 extend the entire length of the compressible member 722 (and extends across the proximal section 723 of the compressible member 722) as shown in FIG. 9. The compressible member 722 can also be a fluid-sealed or a self-contained structure that can be placed over the inner lumen 704 through the lumen 742. The compressible member 722 thus can have two lumens, one for the fluid injection or withdrawal and one for disposing over the inner member 704. Further, the compressible member 722 and the outer member 706 can share a coaxial lumen that can be configured to provide the fluid injection or withdrawn.

The compressible member 722 may extend the entire length of the deliver system 700. The entire length of the compressible member 722 need not contain the pleated section 725 (the bellow section) but may include such section in certain embodiments. As shown in FIG. 9, the more proximal portion 723 of the compressible member 722 need not include a pleated section 725. The portion 723 of the compressible member 722 may provide the lumen path 744 for the injection of fluid into the compressible member 722.

Fluid can be injected into the compressible member using methods known in the art that are used to inflate a conventional balloon. For instance, a fluid supply (not shown) is provided that is in fluid communication with the lumen 744 that enables fluid to be injected into the compressible member 722. A handle (not shown) is typically coupled to the system 700 that enables fluid to be injected therethrough. Fluid such as air, gas, liquid, solution, saline, water, etc., can be used to fill the compressible member 722 in order to expand the compressible member 722. The fluid fill expands the pleated section 725 (e.g., like expanding an accordion structure). The compressible member 722 thus can expand (or at least the pleated section 725 can expand) in the proximal direction D701 and slide on the outer surface of and over a portion of the inner member 704. Thus, when the compressible member 722 is filled with fluid, the compressible member 722 is expanded in the proximal direction D701 dragging with the compressible member 722 the retractable sheath 708 causing the sheath 708 to retract in the proximal direction D701.

In one embodiment, the compressible member 722 is a preferably a non-radially compliant structure so that the compressible member 722 can expand axially.

The expansion of the compressible member 722 can be constrained radially by the inner diameter of the retractable sheath 708 and/or the inner diameter of the outer member 706 as previously mentioned. Thus, when the compressible member 722 is expanded (e.g., by fluid application), the retractable sheath 708 limits the radial expansion but allows the axial expansion of the compressible member 722. The compressible member 722 thus need not be a radially non-compliant structure.

In one embodiment, a lubricious or slippery coating (not shown) is applied over the outer surface of the inner member 704 to facilitate the sliding of the compressible member 722 on the outer surface of the inner member 704.

A proximal adapter (not shown) is coupled to the delivery system 700 that allows for the injection of fluid into the compressible member 722. Many devices known in the art can be coupled to a catheter system to create a positive or negative pressure in the system such as a syringe. In the present example, to inject fluid into the compressible member 722, the syringe is used to inject the fluid into the system 700.

The inner member 704 can include a lumen that accommodates a guidewire 712. The guidewire 712 helps maneuver the delivery system 700 to the treatment site. In one embodiment, the guidewire 712 is stabilized by the inflation of the compressible member 722 during delivery. The inflation of the compressible member 722 may compress the inner member 704 of the delivery system 700 thus coupling the inner member 722 closer to the guidewire 712. This helps stabilize the delivery system 700 and improves the column strength of the inner member 704 during sheath retraction.

Figure 10:
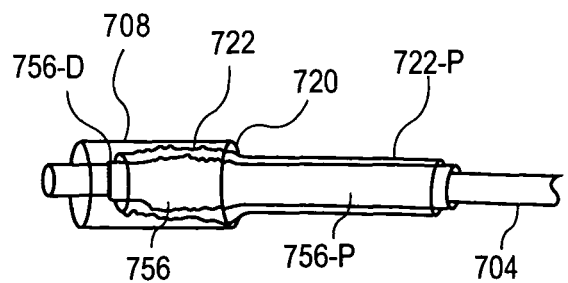
Figure 11:
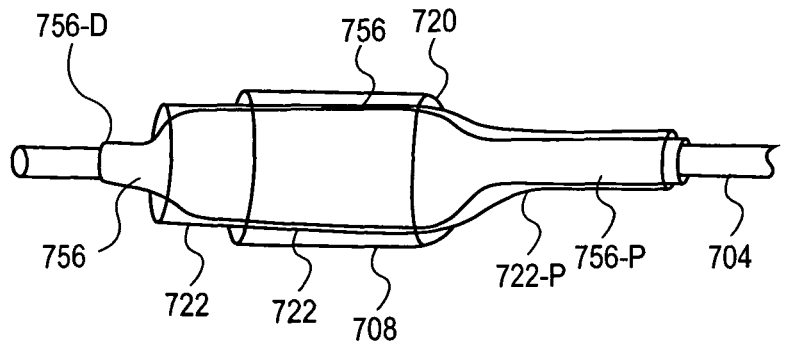

In yet another embodiment, the compressible member 722 of the delivery system 700 can be expanded by a conventional balloon 756 (FIGS. 10-11). In some situations, a suitable compressible member 722 may not be commercially available. A particular desired shape for the compressible member 722 can be achieved by using a conventional balloon to axially expand the compressible member 722 to the desired shape or size. In one embodiment, a suitable balloon 756 is placed under the compressible member 722 and over the inner member 704 as shown in FIG. 10. The balloon 756 is fixed or adhered to the inner member 704 at the balloon distal portion 756-D. In this way, when the balloon 756 is inflated, the balloon 756 is still anchored on the inner member 704. When the balloon 756 is inflated, as shown in FIG. 11, the compressible member 722 is expanded. The balloon 756 may also include a proximal portion 756-P, which can provide an access path for inflating the balloon 756, for example, with fluid or air. In FIG. 10, all components are similar to those shown in FIGS. 7A-7B. For ease of illustration, these components are not shown in FIGS. 10-11. It is to be understood that these components are to be included in this system where a balloon 756 is included to help expand the compressible member 722.

In one aspect, the balloon 756 is a non-compliant balloon, thus, when inflated, the balloon 756 expands the compressible member 722 both axially as well as radially. However, to effectively retract the retractable sheath 708, the expansion of the compressible member 722 is controlled to allow the compressible member 722 to expand only in the axial direction so that the retractable sheath 708 can be retracted.

In one embodiment, the compressible member 722 is a radially non-compliant structure. One advantage of this characteristic is that when inflated or expanded by the balloon 756, the compressible member 722 expands axially and not radially, or at least not substantially radially. The compressible member 722 is contemplated to be axially compliant. Suitable methods known in the art can be used to construct a compressible member 722 that can only expand axially and not radially. Another advantage of having the compressible member 722 being radially non-compliant is that the compressible member 722 is prevented from potentially immobilizing the retractable sheath 708 by pressing against the inner surface of the retractable sheath 708 as the compressible member 722 is expanded during the sheath 708 retraction process. In another embodiment, the compressible member 722 is both radially and axially compliant. The radial expansion of the compressible member 722 can be controlled by the retractable sheath 708 in the present embodiment. The compressible member 722 is disposed within the retractable sheath 708 such that when expanded, the compressible member 722 expands axially to cause the sheath 708 to retract.

In an alternative embodiment, the retraction of the sheath 708 is controlled through a volume control of the fluid that is introduced into the compressible member 722 to expand the compressible member 722 and retracts the sheath 708. The retraction rate of the sheath 708 (as well as the expansion of the compressible member 722) corresponding to a particular rate of fluid injection into the compressible member 722 (or the balloon that is used to expand the compressible member 722) is first determined. Then, based upon the rate of expansion of the compressible member 722, the rate of the fluid injection is controlled so that the sheath 708 can be retracted in a controlled manner. For instance, if it is determined that the injection of 1 mL/sec of fluid results in 1 mm/sec of sheath 708 pullback, the fluid can be introduced into the compressible member 722 at 1 mL/sec at a time to obtain a corresponding 1 mm/sec pullback of the sheath 708. With such control, the problem of abrupt introduction or deployment of the medical device (e.g., the stent 702) is minimized (e.g., minimizing stent jumping). Of course, a particular rate may vary depending on the sizes and dimension of the components as well as the materials of the components of the system 700.

It is contemplated that the system 700 includes a medical device, which is supported by the inner member 704 and is covered by the retractable sheath 708 during delivery. When the retractable sheath 708 is withdrawn, the medical device is exposed or additionally, deployed. The medical device can be a stent 702. The stent 702 can be compressed or collapsed and placed on the outside of the inner member 704 and covered by the retractable sheath 708. Withdrawal or retraction of the retractable sheath 708 would allow the stent 702 to be expanded and deployed. The stent 702 can be a self-expanding structure and as such, the retraction of the retractable sheath 708 would allow the stent 702 to return to its uncollapsed or non-compressed state and be deployed in a vessel. The stent 702 can be made of a shape memory material such as Nickel Titanium (NiTi or Nitinol), a superelastic material, or a polymeric self-expanding material.

The stent 702 can be deployable by a balloon and in such embodiment, a balloon (not shown) is provided underneath the stent 702. The balloon is configured to be inflated as is known by the art. Inflation of the balloon would allow the stent 702 to expand after the retractable sheath 708 is retracted or withdrawn.

In one embodiment, a stopper 710 is provided on the outer surface of the inner member 704 (FIGS. 7A-7B). The stopper 710 can be an O-ring, an annular collar, or a fixture placed on the out side of the inner member 704. The stopper 710 is placed at the proximal end of the stent 702 and distally to the distal end of the compressible member 722. The stopper 710 functions to prevent the compressible member 722 from sliding toward the stent 702 during the retraction of the sheath 708. The stopper 710 can also be a structure that can anchor or fix the compressible member 722 onto the outer surface of the inner member 704. The stopper 710 also prevents the stent 702 from sliding proximally on the inner member 704 during the delivery process. When the stent 702 is in its compressed, collapsed, or undeployed state, the stopper 710 is slightly bigger than the stent 702 to prevent the stent 702 from sliding in the proximal direction D701. When the stent 702 is fully deployed, the stent 702 needs not be stopped by the stopper 710 since it is already deployed against a vessel wall. The stent 702 is deployed against an inner wall of the vessel or the lumen. After the stent 702 is deployed, the delivery system 700 may be withdrawn.

As described above, the stent 702 can be coated with antiproliferate agent to control the cell growth over the stent 702 once it is implanted into a lumen. The stent 702 can be deployed into a vessel such as the artery (not shown) that has a vulnerable plaque section in a manner that the stent 702 opposes the vulnerable plaque section. After the implantation, the stent 702 promotes cell growth over the struts (not labeled) of the stent 702 and hence over the vulnerable plaque section or the fibrous cap of the vulnerable plaque. The cell layer acts to protect the vulnerable plaque from rupturing and possibly occluding the artery. The cell growth may need to be controlled so that uncontrolled cell growth does not occur and in turn occlude the artery. The stent 402 is thus coated with an antiproliferate agent that can control the cell growth over the struts of the stent 702. Examples of an antiproliferate agent includes Taxol, Everolimus, and Sirolimus.

Again, other medical devices can also be delivered by the delivery system 700. Devices such as a Mitral Valve repair device, a stent-graft, a graft, a camera, a diagnostic device, or other therapeutic devices can also be configured so that each can be supported by the inner member 704 and delivered by the system 700 wherein retracting the retractable sheath 708 would allow the device to be deployed or exposed. The retractable sheath 708 can be actuated after being retracted to slide back over the inner member 704 and optionally cover the medical device supported by the inner member 704. In one embodiment, the actuation direction of the retractable sheath 708 is opposite from the direction of retraction (e.g., direction D701). To actuate the retractable sheath 708, the compressible member is axially expanded. If to retract the retractable sheath 708, the compressible member 722 was axially expanded, then to actuate the retractable sheath 708, the compressible member 722 is compressed. Similarly, if to retract the retractable sheath 708, the compressible member 722 was axially compressed, then to actuate the retractable sheath 708, the compressible member 722 is expanded.

Figure 12:
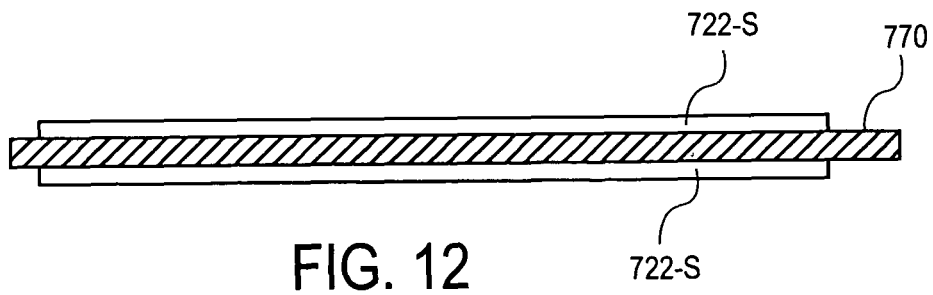
FIGS. 12-13 illustrate exemplary configurations of a compressible member during a process of making the compressible member.
Figure 13:
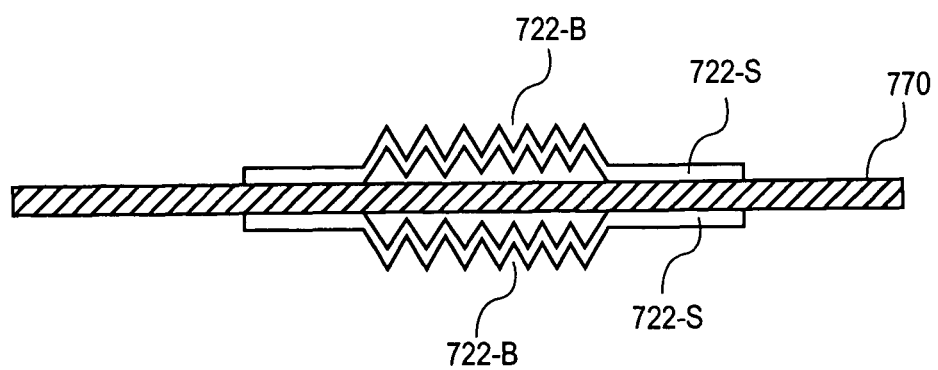

FIGS. 12-13 illustrate an exemplary process of making a compressible member that can be incorporated into the delivery device 700. In one embodiment, the compressible member is a structure that includes a pleated section or a bellow section. In one embodiment, a slide tube 722-S is placed over a mandrel 770. The slide tube 722-S ultimately forms the compressible member 722. The outer diameter of the mandrel 770 has a dimension that is as close as possible to the inner diameter of a lumen provided in the slide tube 722-S. The slide tube 722-S can include one or more lumens as needed. The mandrel 770 is inserted within one lumen provided in the tube 722-S. In one embodiment, the tube 722-S includes a thermoplastic, melt processible, polyether-based polyamide material such as PEBAX®, which a registered trademark of Atochem Corporation. Other polymer or fluoropolymer resins such as Polytetrafluoroethylene (PTFE), Fluorinated Ethylene Polymer (FEP), Perfluoroalkoxy (PFA), Ethylene Tetrafluoroethylene (ETFE), and Polyetheretherketone (PEEK) can also be used. The tube 722 is compressed as shown in FIG. 13. Additional mandrels can be inserted into other lumens in the tube 722-S to keep the lumens open after the compressible member 722 is formed. Under the compressed state, the tube 722-S is scrunched over the mandrel 770. The scrunched tube 722-S is then heat treated for a few seconds. The tube 722-S is then formed with a pleated or bellow section 722-B. The mandrel 770 is thereafter removed. The tube 722-S can also be treated (compressed and heat treated) while inside another sheath (e.g., the outer member 706) in order to control the desired outer diameter of the compressible member 722.

In an alternative approach, the compressible member 722 is placed in an expanded state during delivery and axially compressed to cause the retraction of the retractable sheath 708. The present embodiment comprises all the components previously described for the delivery system 700. Similar to above, the delivery system 700 shown in FIGS. 14A-14B includes the guidewire 712 disposed within the inner member 704, which is disposed within the outer member 706. The stent 702 is disposed on the outer surface of the inner member 704 as previously described. In the delivery state, the stent 702 is compressed and contained by the retractable sheath 708. In this configuration, the compressible member 722 is axially expanded. The compressible member 722 is connected to the retractable sheath 708 at a point or points 790. A portion of the pleated section of the compressible member 722 is disposed within the retractable sheath 708. In the present embodiment, the distal portion of the compressible member 722 is not fixed onto the inner member 704 as previously described in FIGS. 7A-7B. Instead, a proximal portion of the compressible member 722 is fixed on the outer surface of the inner member 704. The stopper 710 prevents the stent 702 from moving proximally in the direction D701 during retraction of the sheath 708 as previously discussed. To actuate the compressible member 722, it is inflated with a fluid.

Figure 14A:
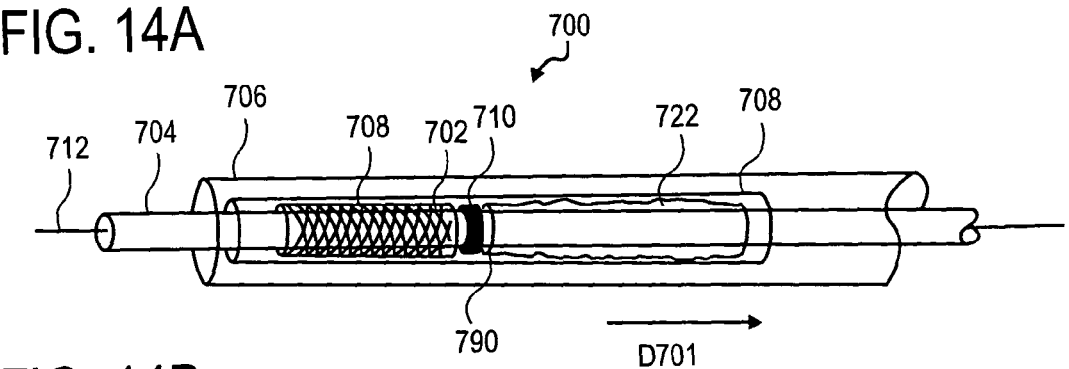
FIGS. 14A-14B and 15A-15B illustrate exemplary embodiments of a delivery system of the present invention that employs a compressible member to withdraw a sheath.
Figure 14B:
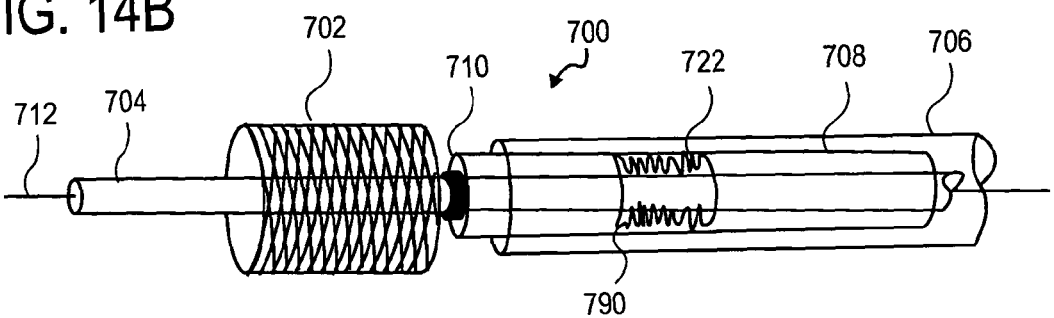

In the initial state, when the delivery system 700 is in its delivery state, the compressible member 722 is axially expanded as shown in FIG. 14A. To begin retracting the sheath 708, fluid is withdrawn from the compressible member 722 to axially compress the compressible member 722 in the proximal direction D701 as shown in FIG. 14B. As the fluid is withdrawn proximally, the compressible member 722 axially compresses proximally, and the retractable sheath 708 is retracted proximally. The apparatus can be equipped with a proximal adapter with a hydraulic action capability (not shown) which is coupled to the delivery system 700 to supply fluid into the compressible member 722 for delivery and to withdraw fluid from the compressible member 722 to compress the compressible member 722 to thereby retract the retractable sheath 708. As before, fluid can also be air or a liquid. Upon retraction of the sheath 708, the stent 702 is exposed and expanded as previously described. Again, other medical devices can replace the stent 702.

Figure 15A:
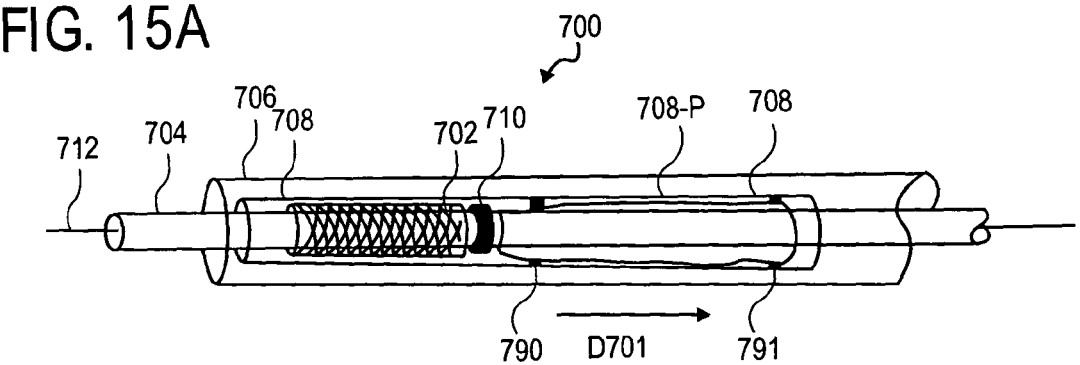
Figure 15B:
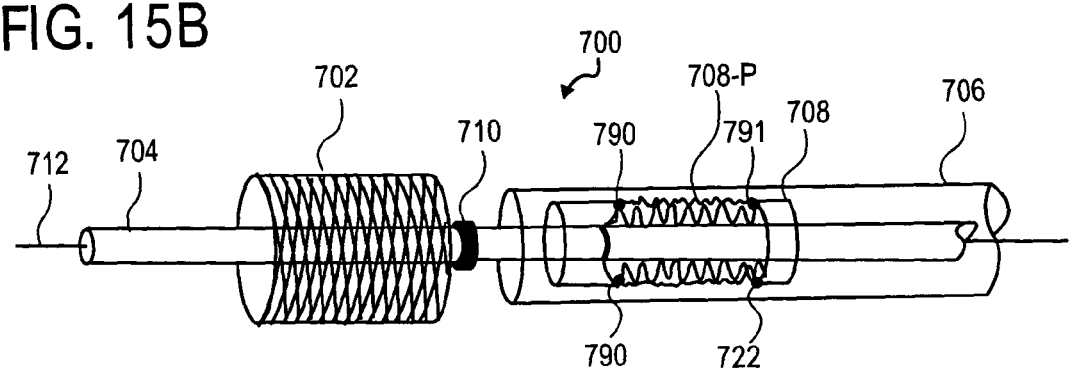

In an alternative embodiment, the retractable sheath 708 may be configured so that the sheath 708 also has a pleated section as so to allow the sheath 708 to retract along with the axially compression of the pleated section. In FIG. 15A, the compressible member 722 is in its expanded state. The compressible member 722 is connected to the sheath 708 at the points 790 and 791. A portion of the compressible member 722 resides within the retractable sheath 708. The sheath 708 further includes a pleated or bellow section 708-P. The bellow section 708-P of the retractable sheath 708 can align with the bellow section of the compressible member 722 as shown in FIG. 15B. To retract the retractable sheath 708, the compressible member 722 is deflated and axially compressed like an accordion also causing the sheath section 708-P to compress therewith. This action drags the sheath 708 in the proximal direction D701. Upon retraction of the sheath 708, the stent 702 is exposed and expanded (FIG. 15B) as previously described.

The retraction of the retractable sheath 708 can be controlled through a volume control of the fluid that is withdrawn from the compressible member 722 to compress the compressible member 722 and retract the retractable sheath 708. In one aspect, the retraction rate of the retractable sheath 708 (as well as the rate of compression of the compressible member 722) corresponding to a particular rate of fluid withdrawal is first determined. Then, based upon the rate of compression of the compressible member 722, the rate of the fluid withdrawal is controlled so that the sheath 708 can be retracted in a controlled manner. For instance, if it is determined that the withdrawal of 1 mL/sec of fluid results in 1 mm/sec of sheath 708 pullback, the fluid can be withdrawn from the compressible member 722 at 1 mL/sec at a time to obtain a corresponding 1 mm/sec pullback of the sheath 708. With such control, problem of abrupt introduction or deployment of the medical device (e.g., the stent 702) is minimized.

FIGS. 16-18 illustrate yet another exemplary embodiment of a delivery system 1600 that can deploy a medical device in a tortuous pathway. In the present embodiment, a compliant balloon system is configured so that the balloon, which axially elongates with increasing pressure (e.g., caused by fluid or air pressure), is used to facilitate deployment of the medical device. A compliant balloon is one that does not retain its shape upon being inflated. In comparison, a non-compliant balloon is one that retains its shape as it is inflated. For instance, the balloon is preshaped so that when inflated, the balloon only inflates to the predetermined shape. The compliant balloon system of the delivery system 1600 is mechanically connected to a retractable sheath that constraints a medical device during delivery similar to previously described. The elongation of the compliant balloon results in an axial motion of the retractable sheath thus retracting the sheath back to expose and/or deploy the medical device. A constraint member is further disposed outside the balloon system. The constraint member defines an radial expanding limit for the balloon system, thus, restricting growth of the balloon to the axial direction. The sheath is retracted when the compressible member is expanded. Additionally, the delivery system may also include a spring system or member that allows the delivery system to withstand high compressive force while still providing high flexibility. Such flexibility prevents buckling or kinking of the delivery system during delivery or retraction of the sheath to deliver the medical device. This feature is particularly useful when the delivery system has to go through tortuous pathways.

FIGS. 16-18 illustrate the delivery system 1600 in more detail. The system 1600 comprises an outer member 1006, an inner member 1004 disposed within the outer member 1006, a retractable sheath 1008 disposed over at least a portion of the inner member 1004, and a compressible member 1022 mechanically connected to the sheath 1008. In one embodiment, the compressible member 1022 acts as the retraction member with the assistance of a balloon system. A constraint member 1030 is placed on the outside of the compressible member 1022 to define the radial expansion limit of the compressible member 1022. The sheath 1008 is used to initially maintain a medical device or a stent 1002 in an unexposed, crimped, or undeployed position. The stent 1002 is supported by the inner member 1004 for the delivery.

It is contemplated that the compressible member 1022 can be a compliant and inflatable balloon. The balloon may be inflated by fluid pressure (e.g., using gas, air, liquid, or solution). Initially, during delivery, the compressible member 1022 is deflated as shown in FIG. 16. Once the delivery device 1600 has reached the treatment site where the stent 1002 is to be deployed, the compressible member 1022 is inflated or expanded as shown in FIG. 17. The constraint member 1030 constrains the radial expansion of the compressible member 1022 (the balloon) in the radial direction. The constraint member 1030 is a non-compliant structure. During inflation, the compressible member 1022 is thus free to expand and elongate toward the proximal section of the delivery system 1600.

At the distal end of the compressible member 1022 is a first stopper 1010, which is bonded to the inner member 1004 and acts to constrain the expansion of the compressible member 1022 in the distal direction D1003. The first stopper 1010 may be placed within the constraint member 1030 as shown in FIG. 16. At a proximal end of the compressible member 1022 is a second stopper 1032 acts to separate a spring member 1036 and the compressible member 1022. The second stopper 1032 may be placed within the constraint member 1030 as shown in FIG. 16. Alternatively, the constraint member 1030 may be shorter and one or both of the stoppers 1010 or 1032 may be axially located outside of the constraint member. It is preferred that the stoppers 1010 and 1032 be axially located within the constraint member 1030 to confine the radial expansion of the compressible member 1022 within the constraint member 1030. The second stopper 1032 is slideable for a predetermined distance on the outer surface of the inner member 1004.

A spring system 1036 can be placed proximally to the compressible member 1022 and the second stopper 1032. The spring system 1036 provides the delivery system 1600 with a flexible but non-compressible portion. The flexibility of the spring is useful for the insertion of the delivery system 1600 through tortuous vasculature. The spring system 1036 may be connected to the second stopper 1032 that confines the compressible member 1022. Additionally, the spring system 1036 may be placed within the constraint member 1030 as shown in FIGS. 16-17. The spring system 1036 is configured so that it is tightly wound such that not a substantial amount of axial compression will happen when the compressible member 1022 elongates axially during expansion. A third stopper (e.g., a washer) 1034 is connected to the proximal end of the spring system 1036 as shown in FIGS. 16-17. The third stopper 1034 in turn is connected to the sheath 1008 either directly or via a pullwire 1020. In one embodiment, the retractable sheath 1008 extends to the third stopper 1034 and directly connects to the third stopper 1034. The sheath 1008 is contemplated to be placed on the outside of the constraint member 1030. The sheath 1008 also may be shorter and only covers the length of the stent 1002. The sheath 1008 is then connected to the pullwire 1020, which is then connected to the third stopper 1034. The pullwires 1020 also is disposed on the outside of the constraint member 1030. The presence of the constraint member 1030 also protects and/or provides a small space between the compressible member 1022 and the sheath 1008 when the compressible member 1022 is expanding so that the sheath 1008 is not affected by a frictional force. The constraint member 1030 thus protects the compressible member 1022 from the pullwires 1020 in some embodiment and protect the internal wall of the sheath 1022 from the compressible member 1022 in other embodiments.

As the compressible member 1022 expands, the compressible member 1022 elongates toward the proximal portion of the delivery system 1600 in the proximal direction D1001. As the compressible member 1022 elongates, the compressible member 1022 pushes against the stopper or washer 1032 which is connected to the spring system 1036. The spring system transfers the movement of the second stopper 1032 in the proximal direction imparting the elongation of the compressible member to the third stopper 1034. This action causes the sheath 1008 to be retracted in the proximal direction D1001.

The delivery system 1600 also can include a guidewire (not shown) as previously discussed for the maneuvering the delivery system 1600 to the treatment site. In such embodiment, the inner member 1004 may be configured with a lumen to accommodate the guidewire as is conventionally known in the art.

The delivery system 1600 also can include a handle (not shown) having a hydraulic fluid component that can be configured to inject fluid (e.g., air, gas, liquid, or solution) into the compressible member 1022 to expand the compressible member 1022. The injection of fluid can also be controlled with a predetermined expansion rate similar to previously discussed so that the sheath 1008 can be retracted in a controlled manner.

Similar to previous devices, the compressible member 1022 can go from initially being compressed to be axially expanded to cause the retractable sheath 1008 to retract or actuate over the inner member 1004. Alternatively, the compressible member 1022 can go from initially being expanded to be axially compressed to cause the retractable sheath 1008 to retract or actuate over the inner member 1004.

FIG. 18 illustrates still yet another alternative embodiment of a delivery system 1800. The delivery system 1800 is similar to the system 1600 depicted in FIG. 16 in all aspects except that the compressible member 1022 is replaced by a pleated non-compliant inflatable balloon or bellow structure 1050. The pleated structure 1050 provides for more axial compression during delivery than the compressible member 1022 without pleats.

In either delivery system 1600 or 1800, the retraction of the sheath 1008 can be controlled through a volume control of the fluid that is introduced into the compressible member 1022 or the pleated structure 1050 to expand the same. As before, the retraction rate of the retractable sheath 1008 (as well as the rate of expansion of the compressible member 1022 or the pleated structure 1050) corresponding to a particular rate of fluid injection is first determined. Then, based upon the rate of expansion of the compressible member 1022 or the pleated structure 1050, the rate of the fluid injection into the compressible member 1022 is controlled so that the sheath 1008 can be retracted in a controlled manner. Again, with such control, problem of abrupt introduction or deployment of the medical device (e.g., the stent 1002) is minimized.

In the previous embodiments where the device 1002 is a stent, the stent may be a self-expanding stent or a stent expandable by a technique such as using a balloon. When the stent is fully deployed, the stent presses against an inner wall of the vessel or the lumen. The delivery system 1600 or 1800 is then thereafter withdrawn. Other medical devices can also be delivered by the delivery system 1600 or 1800.

FIGS. 19-20 illustrate another approach to a delivery system 1900 that can deploy a medical device in a tortuous pathway. In the present embodiment, a spring system that axially elongates or expands is used to facilitate deployment of the medical device. The spring system is mechanically connected to a retractable sheath. The spring system can retract the retractable sheath as will be discussed below. The elongation of the spring system results in an axial motion of the retractable sheath thus retracting the sheath back to expose and/or deploy the medical device. The compression of the spring system can also result in an axial motion that retracts the sheath to expose and/or deploy the medical device. Moreover, the elongation of the spring system can result in an axial motion that causes the retractable sheath to actuate in the opposite direction and/or cover the medical device. In yet another approach, the compression of the spring system results in an axial motion that causes the retractable sheath to actuate in the opposite direction and/or cover the medical device.

In one embodiment, the delivery system 1900 comprises an outer member 1906, an inner member 1904 disposed within the outer member 1906, a sheath 1908 disposed over the inner member 1904, and a spring member 1922 connected to the sheath 1908 and slideably disposed on the inner member 1904. The sheath 1908 is also slideable over the inner member 1904. The spring member 1922 is axially expandable or allowed to uncoil. The sheath 1908 is mechanically connected to the spring member 1922 such that when the spring member 1922 is allowed to uncoil or expand, the sheath 1908 is retracted.

A first stopper 1910 can be placed at the distal end of the spring member 1922. The first stopper 1910 is bonded to the inner member 1904. The first stopper 1910 constrains one side of the spring member 1922 such that the stopper 1910 prevents the spring member 1922 from sliding distally in the direction D1903.

Further, lock mechanism 1936 is placed at the proximal end of the spring member 1922. The lock mechanism 1936 constrains or compresses the spring member 1922 to prevent the spring member 1922 from uncoiling or axially expanding during delivery. The lock mechanism 1936 is configured so that when the lock is release, the spring member 1922 can expand axially in the proximal direction D1901 as shown in FIG. 20. When the spring member 1922 expands axially in the proximal direction D1901, the sheath 1908 is retracted proximally in the same direction since the sheath 1908 is mechanically connected to the spring member 1922. The sheath 1908 can be connected to the spring member 1922 via a connecting member (e.g., one or more wires or a tube) 1920. One end of the connecting member 1920 is attached to the proximal portion of the spring member 1922 and the other end of the connecting member 1920 is attached to the proximal portion of the sheath 1908. In another approach, the sheath 1908 extends a length that is sufficient to allow it to directly connect to the proximal end of the spring member 1922. The sheath 1908 thus may be long enough to extend from the stent 1902 to the end or the spring member 1922. The sheath 1908 thus may have the spring member 1922 disposed there within.

In one embodiment, the spring member 1922 includes a washer 1934 placed at the proximal end of the spring member 1922. In the present embodiment, the sheath 1908 is connected to the spring member 1922 via the washer 1934.

FIGS. 21-32 illustrate exemplary embodiments of lock mechanisms that can be used for the lock mechanism 1936 to hold the spring member 1922 of the delivery system 1900 in its compressed state until the sheath 1908 is ready to be withdrawn.

Figure 21:
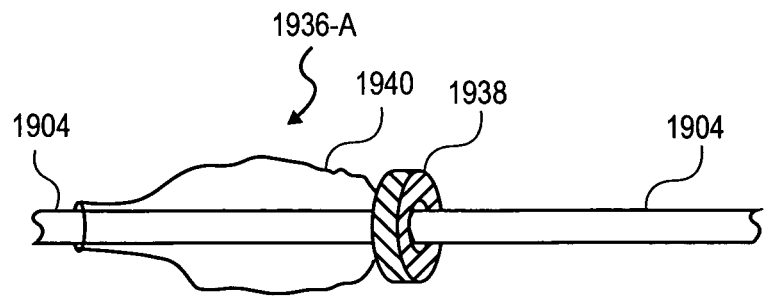
FIGS. 21-32 illustrate exemplary embodiments of a locking system that can be used for a delivery system made in accordance with embodiments of the present invention.
Figure 22:
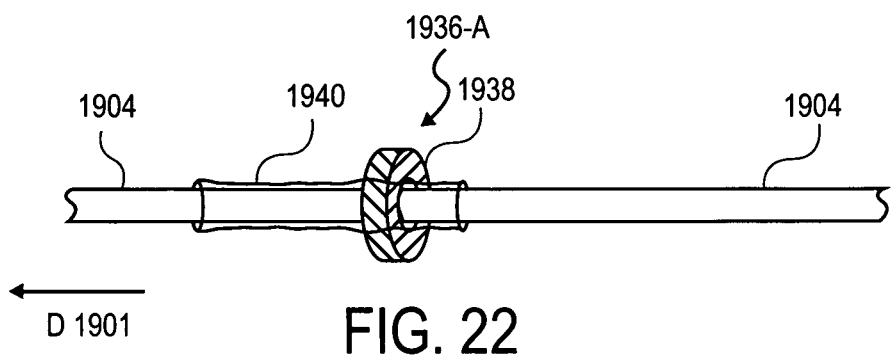

In FIGS. 21-22, a lock mechanism 1936-A including a lock member 1938 and an inflatable balloon 1940 is disposed over the inner member 1904 at a distal position to the inflatable balloon 1940. In an initial state, the lock mechanism 1936-A is configured and positioned so that it can constrain the spring member 1922 in a compressed state as shown in FIG. 19. In the initial state, the lock member 1938 is positioned proximal to the spring member 1922. The inflatable balloon 1940 of the lock mechanism 1936-A is inflated as shown in FIG. 21. The inflatable balloon 1940 may include a lumen to allow for the inflation of the balloon. The lock member 1938 is configured so that it is slideable over the inner member 1904 and the balloon 1940 when the balloon 1940 is deflated. To unlock the spring member 1922, the inflatable balloon 1940 is deflated as shown in FIG. 22. When the balloon 1940 is deflated, the spring member 1922 is no longer constrained and as such will push toward the proximal direction D1901. The lock member 1938 slides over the balloon 1940 allowing the spring member 1922 to expand (as shown in FIG. 20). The expansion of the spring member 1922 drags the sheath 1908 that is connected to the spring member 1922 in the proximal direction D1901 thus exposing or deploying the medical device or the stent 1902.

Figure 23:
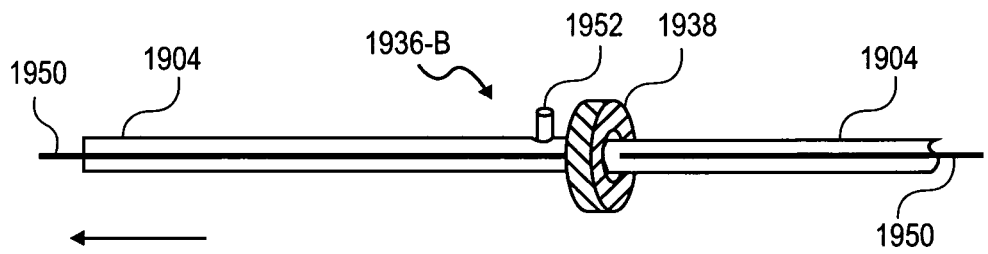
Figure 24:
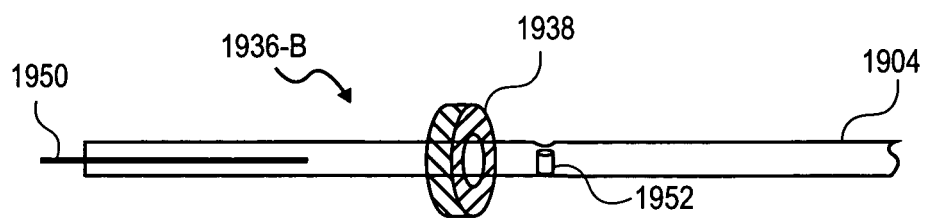

In FIGS. 23-24, there is shown a lock mechanism 1936-B including a lock member 1938, a latch 1952, and a latch release 1950 disposed over or within the inner member 1904. The latch release 1950 may be a wire that is disposed within an inner lumen of the inner member 1904. The latch 1952 is configured to protrude out from the inner member 1904 such that it can limit the movement of the lock member 1938. For instance, the latch 1952 is inserted through an opening created in the inner member 1904 and held in a protruding state by the latch release 1950 that is disposed beneath the latch 1952. The latch release 1950 thus holds the latch 1952 in its protruding state limiting the movement of the lock member 1938. When the latch release 1950 is removed, the latch 1952 withdraws into the inner member 1904 allowing the lock member 1938 to be released. In an initial state, the lock mechanism 1936-B is configured and positioned so that it can constrain the spring member 1922 in a compressed state as shown in FIG. 19. In the initial state, the latch 1952 is in its protruding state so as to hold the lock member 1938 in place as shown in FIG. 23. The lock member 1938 is configured so that it is slideable over the inner member 1904 when the latch 1952 is released. To unlock the spring member 1922 to allow the spring to recoil, the latch release 1950 is removed and the latch 1952 released as shown in FIG. 24. When the latch 1952 is released, the lock member 1938 moves in the proximal direction D1901 allowing the spring member 1922 to expand in the proximal direction D1901. The expansion of the spring member 1922 drags the sheath 1908 that is connected to the spring member 1922 in the proximal direction D1901 thus exposing or deploying the medical device or the stent 1902 (as shown in FIG. 20).

Figure 25:
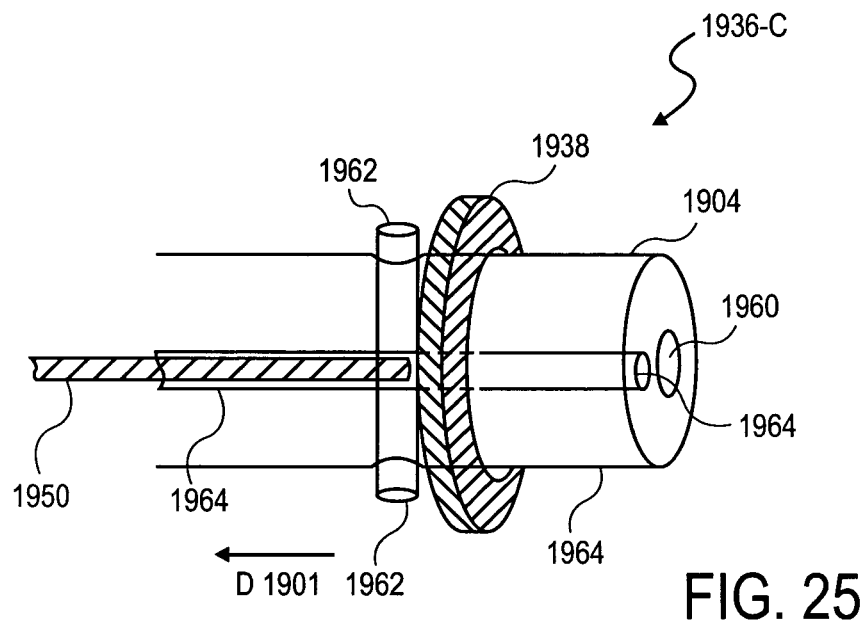
Figure 26:
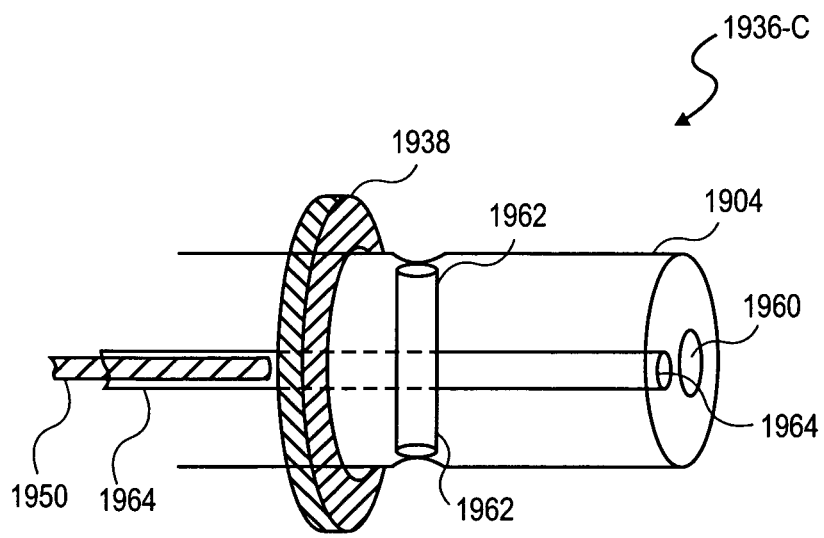

In FIGS. 25-26, a lock mechanism 1936-C including a lock member 1938, a latch 1962, and a latch release 1950 is disposed over the inner member 1904. The lock mechanism 1936-C is similar to the lock mechanism 1936-B except that the latch 1962 may extend out from the inner member 1904 from more than one point (e.g., two points or two projections). The latch release 1950 may be a wire that is disposed within an inner lumen 1964 of the inner member 1904. The inner member 1904 may include more than one lumen, for example, a lumen 1964 for the latch release 1950 and a lumen 1960 is provided for a guidewire (not shown) for the delivery system 1900 (FIGS. 19-20). The latch 1962 is configured to protrude out from the inner member 1904, for example, at two locations, such that it can limit the movement of the lock member 1938. For instance, the latch 1962 may include two pins that are inserted through openings created in the inner member 1904 and held in a protruding state by the latch release 1950 that is disposed beneath the pins. The latch release 1950 thus holds the pins in their protruding state. When the latch release 1950 is removed, the pins withdraw into or slightly below the surface of the inner member 1904 allowing the lock member 1938 to be released. In an initial state, the lock mechanism 1936-C is configured and positioned so that it can constrain the spring member 1922 in a compressed state as shown in FIG. 19. In the initial state, the latch 1962 is in its protruding state so as to hold the lock member 1938 in place as shown in FIG. 25. The lock member 1938 is configured so that it is slideable over the inner member 1904 when the latch 1962 is released. To unlock the spring member 1922, the latch release 1950 is removed and the latch 1962 released as shown in FIG. 26. When the latch 1962 is released, the lock member 1938 moves in the proximal direction D1901 allowing the spring member 1922 to expand in the proximal direction D1901. The expansion of the spring member 1922 drags the sheath 1908 that is connected to the spring member 1922 in the proximal direction D1901 thus exposing or deploying the medical device or the stent 1902 (as shown in FIG. 20).

Figure 27:
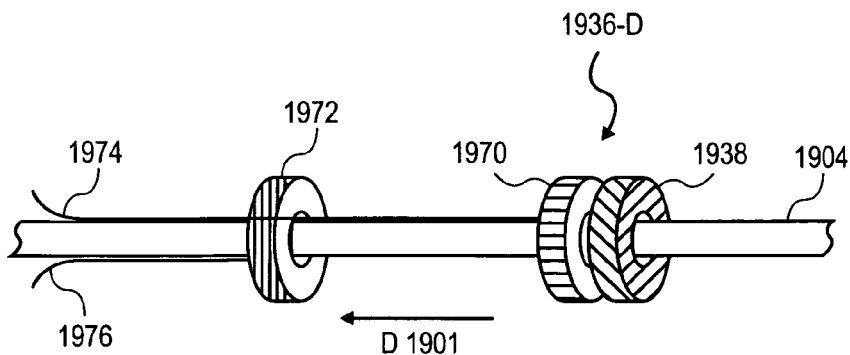
Figure 28:
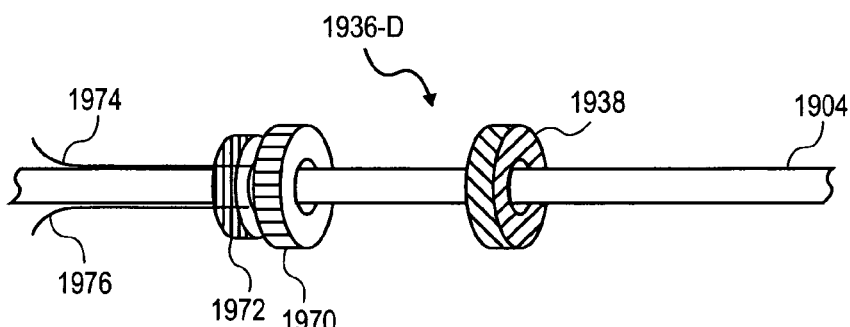

In FIGS. 27-28, a lock mechanism 1936-D is disposed over the inner member 1904. The lock mechanism 1936-D utilizes an electromagnetic system to lock and release the spring member 1922. In one embodiment, the lock mechanism 1936-D includes a lock member 1938, a first electromagnetic member 1970, a second electromagnetic member 1972, a first coupling 1974, and a second coupling 1976. Each of the first electromagnetic member 1970 and the second electromagnetic member 1972 is charged so that in the initial state, they repel each other such that the first electromagnetic member 1970 prevents the lock member 1938 from moving proximally in the proximal direction D1901. In the initial state, the lock member 1938 thus constrains the spring member 1922 in the unexpanded position (FIG. 19). The first coupling 1974 and the second coupling 1976 are used to create the appropriate charges in the first electromagnetic member 1970 and the second electromagnetic member 1972. In the initial state, the first electromagnetic member 1970 is positively (+) or negatively (−) charged and the second electromagnetic member 1972 is likewise positively (+) or negatively (−) charged. The first and second electromagnetic member 1970 and 1972 have the same charges in the initial state. To release the lock member 1938 so as to allow the spring member 1922 to expand axially, the first electromagnetic member 1970 and the second electromagnetic member 1972 are charged so that they have opposite charges to one another. For instance, the first electromagnetic member 1970 may be positively (+) charged and the second electromagnetic member 1972 negatively (−) charged. The opposite charges cause the first electromagnetic member 1970 to slide toward the second electromagnetic member 1972 as shown in FIG. 28. This action releases the lock member 1938 thus allowing the spring member 1922 to expand (as shown in FIG. 20).

In one embodiment, the second electromagnetic member 1972 may be bonded to the inner member 1904 and is not movable or slideable on the inner member 1904. The first electromagnetic member 1970 is configured to be slideable on the inner member 1904. This way, the first electromagnetic member 1970 would slide toward the second electromagnetic member 1972 and not the other way around to release the lock member 1938. The first electromagnetic member 1970 can also function as the lock member 1938 thus the lock member 1938 is not needed. The repelling force in the initial state is sufficient so that the first electromagnetic member 1970 and the second electromagnetic member 1972 can cause the spring member 1922 to stay in the compressed configuration. The expansion of the spring member 1922 drags the sheath 1908 that is connected to the spring member 1922 in the proximal direction D1901 thus exposing or deploying the medical device or the stent 1902 (as shown in FIG. 20).

Figure 29:
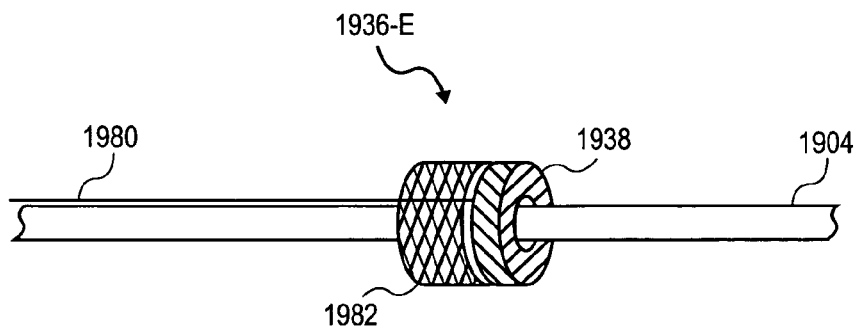
Figure 30:
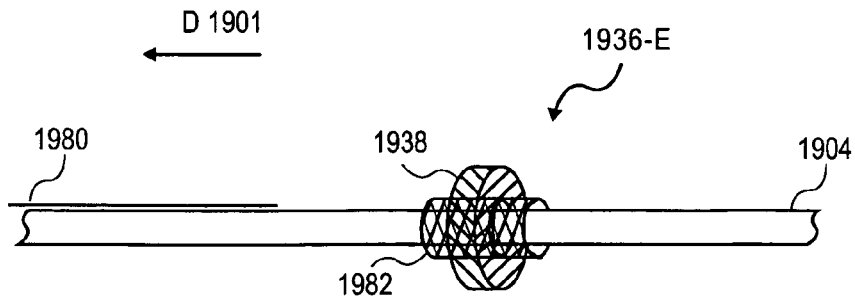

In FIGS. 29-30, a lock mechanism 1936-E is disposed over the inner member 1904. The lock mechanism 1936-E includes a lock member 1938, a compressible/foldable member 1982, and a folding mechanism 1980. In the initial state as shown in FIG. 29, the compressible member 1982 is fully expanded thus holding the lock member 1938 in place. The compressible member 1982 is coupled to the folding mechanism 1980 such that the folding mechanism 1980 can cause the collapsing or folding of the compressible member 1982. In one embodiment, the compressible member 1982 is a foldable basket that is configured to be disposed on the inner member 1904. The basket may include a wire that acts as the folding mechanism 1980 that extends therefrom. When the wire is pulled on, the basket collapses causing the release of the lock member 1938 as shown in FIG. 30. When the compressible member 1982 is collapsed, the lock member 1938 is released, the spring member 1922 is no longer constrained and as such will push toward the proximal direction D1901. The lock member 1938 slides over the compressible member 1982 allowing the spring member 1922 to expand (as shown in FIG. 20). The expansion of the spring member 1922 drags the sheath 1908 that is connected to the spring member 1922 in the proximal direction D1901 thus exposing or deploying the medical device or the stent 1902.

Figure 31:
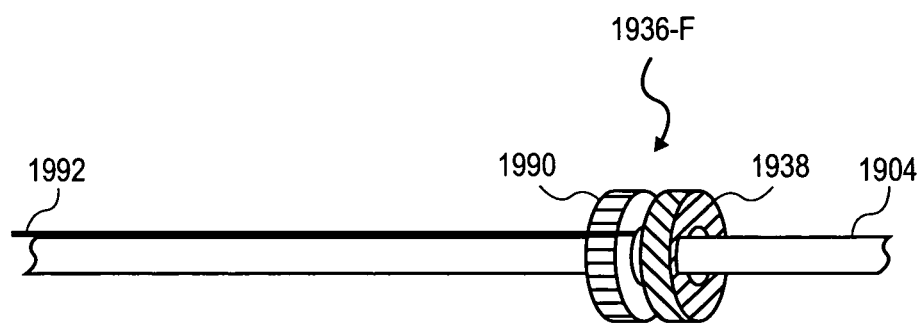
Figure 32:
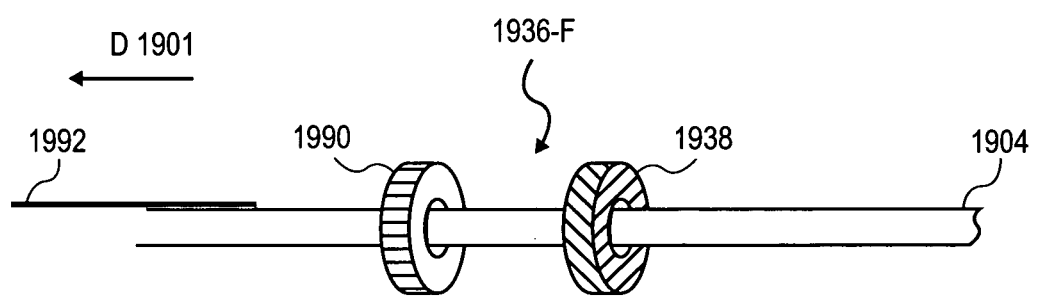

In FIGS. 31-32, instead of using a compressible member 1982 of the lock mechanism 1936-E as previously described, a lock member 1938 is held in place simply by a wire 1992 and a ring 1990 disposed on the inner member 1904. When the wire 1992 is removed, the ring 1990 slides in the proximal direction D1901 allowing the lock member 1938 to be released. The ring 1990 is configured so that when it is disposed over the inner member 1904, it constrains the movement of the lock member 1938 in the proximal direction D1901 when the wire 1992 is connected thereto. It may be that the ring 1990 is sized so that when it is disposed over the inner member 1904, there is a gap sufficient for the wire 1992 to be inserted therein and holds the ring 1990 in place as shown in FIG. 31. Other ways of holding the ring 1990 in place can also be used. When the wire 1992 is removed, the gap allows sufficient space for the ring 1990 to slide over the inner member as shown in FIG. 32. When the wire 1992 is removed, the ring 1992 moves in the proximal direction D1901 allowing the lock member 1938 to be similarly moved and allowing the spring member 1922 to expand axially. The expansion of the spring member 1922 drags the sheath 1908 that is connected to the spring member 1922 in the proximal direction D1901 thus exposing or deploying the medical device or the stent 1902. In other embodiment, the lock member 1938 may be eliminated altogether and the ring member 1990 alone can hold the spring member 1922 in the compressed state until the wire 1992 is removed.

In any of the embodiments described, a lubricious or slippery coating is applied over the inner member 1904 to facilitate the sliding of the lock member and/or the spring member over the inner member 1904.

In certain of the disclosed embodiments, the spring member 1922 can be held in an uncompressed or uncoiled state during the initial state or the delivery state. When the spring 1922 is compressed axially, the sheath is retracted. These mechanisms are similar to the embodiments discussed associated with FIGS. 14A-14B and 15A-15B.

A proximal adapter (not shown) is coupled to the delivery system 1900 that allows for the manipulation of the lock mechanism 1936.

Figure 33:
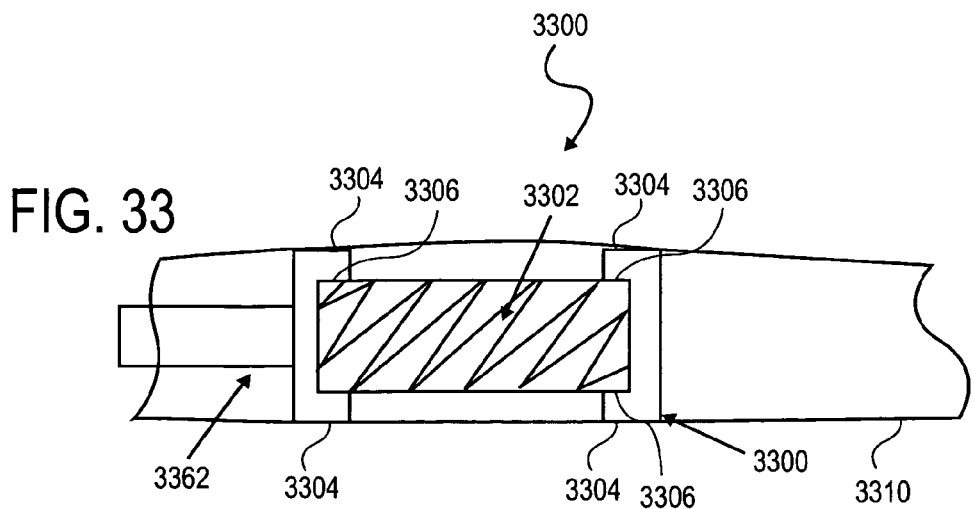
FIGS. 33-35 illustrate an exemplary embodiment of a delivery system that uses a balloon to hold a stent in an undeployed state.
Figure 34:
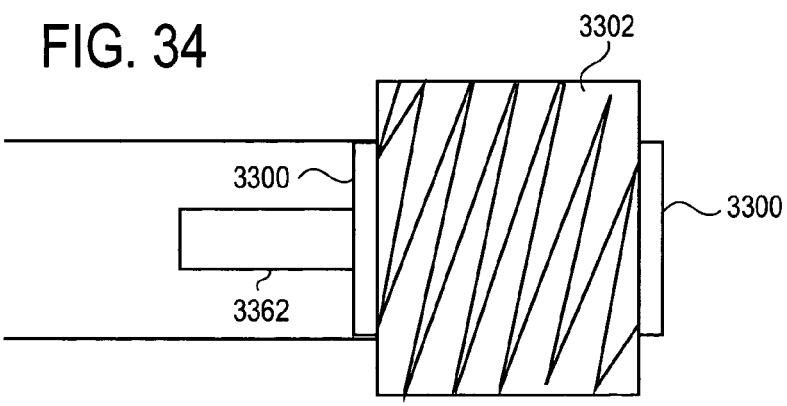
Figure 35:
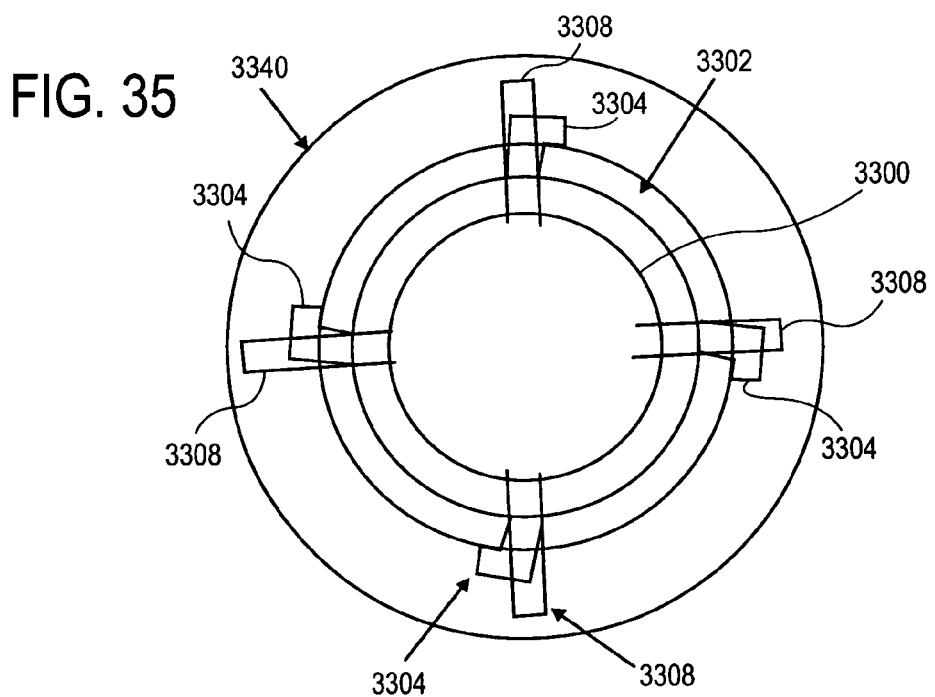

We turn now to FIGS. 33-35 which illustrate an exemplary embodiment of the invention where a sheath that holds a medical device during the delivery state is itself expandable. The sheath thus can be referred to as an expandable member. The sheath is configured so that when the sheath is not fully expanded, the sheath is capable of holding the medical device in an undeployed state and that when the sheath is expanded, the sheath releases the medical device for deployment once delivery is achieved.

As shown in FIGS. 33-34, a delivery device 3300 for a medical device 3302 comprises an outer member 3310, a delivery member 3362 disposed within the outer member 3310, and an expandable member 3300 configured to have prongs (latches, wings or extensions) 3304 when in non-fully inflated state and no prongs when fully inflated. The prongs 3304 of the expandable member 3300 are configured to hold the medical device 3302 in a non-deployed state when the expandable member 3300 is in the non-fully inflated state. The expandable member 3300 is further coupled to the delivery member 3362. As before, the medical device 3302 can be a stent, expandable or self-expandable.

The expandable member 3300 is a balloon with prong or latches 3304 that clamp down on the medical device 3302 and prevent deployment, exposure, or expansion of the medical device 3302 until the balloon and its latches are inflated or fully inflated. When the balloon is inflated, the prongs 3304 are inflated and extended straight out so that the prongs 3304 are no longer acting as prongs or latches that can clamp down on the medical device 3302. When inflated, the balloon obtains a straight configuration and as such, allowing the medical device to deploy. Should the device 3302 be a stent, when the balloon is inflated or fully inflated, the stent can expand either by self-expanding (due to the stent's design and/or material) or by using other methods known in the art as previously mentioned. For instance, in one embodiment, a balloon can be disposed under the stent and used to expand the stent as is known in the art.

The medical device 3302 can be disposed on the outer surface of the delivery member 3362. The medical device 3302 is placed so that it only rides on or is supported by the delivery member 3362 during delivery. When the device 3302 is deployed, it may be deployed against the wall of a vessel. The delivery member 3362 is then no longer supporting the device 3302 and thus, can be withdrawn from the vessel. An example of such a medical device is a stent or a self-expanding stent.

FIG. 35 illustrates a cross-sectional view of the expandable member 3300 and the medical device 3302. As can be seen, when the expandable member 3300 is not fully inflated, the prongs 3304 are present and able to constrain the medical device 3302. As stated, when the expandable member 3300 is fully expanded, the prongs 3304 become straightened or flattened as illustrated by references 3308. The medical device 3302 is no longer constrained at this point and can be expanded or deployed as previously described.

The expandable member 3300 can include coupling members such as adhesive features 3306 disposed between the prongs 3304 and the device 3302. For instance, adhesive balls 3306 can be disposed on the outside surface of the device 3302 to enhance the coupling between the prongs 3304 and the medical device 3302. When pressure is used to inflate the inflatable member 3300, the coupling between the adhesive balls 3306 and the device 3302 is broken allowing the device to expand. The expandable member 3300 can be included or incorporated into anyone of the exemplary devices of the present invention. The expandable member 3300 can be incorporated into a retractable sheath of a section of the retractable sheath to confine the medical device. Alternatively, a section of the retractable sheath can be configured similarly to the expandable member 3300 (e.g., with prongs that when the sheath is inflated, release the medical device as previously discussed).

In one embodiment, to deliver a device to a treatment site using an exemplary embodiment of the present invention, one carries out the following method. First, a medical device is releasably coupled to a delivery member. As mentioned above, the medical device is supported by the delivery member and may only need to ride on the outer surface of the delivery member. The medical device can be a stent in its compressed state during delivery. Next, a sheath is releasably coupled over the medical device so as to constrain the medical device during delivery. The delivery member is then tracked or advanced to a treatment site. The medical device, the delivery member, are disposed within an outer member as previously described. The sheath is withdrawn to expose and/or deploy the medical device at the treatment site as previously discussed. The sheath is coupled to a sheath release system that is selected from a group consisting of a flexible intermediary member, a compressible member, a spring member, and an expandable member (previously described) such that when the sheath is being withdrawn, the delivery system is substantially free from buckling, folding, or bending.

In another embodiment, to deliver a device to a treatment site using an exemplary embodiment of the present invention, one carries out the following method. First, a medical device is advanced to a treatment site. The medical device is supported by an inner member and constrained by a retractable sheath during advancement. The retractable sheath is slideable over the inner member. The medical device, the inner member, and the retractable sheath are disposed within an outer member. A flexible intermediary member is provided and bonds the retractable sheath to the outer member. The flexible intermediary member is foldable within the outer member. Next, the retractable sheath is retracted by causing a negative pressure between the outer member and the flexible intermediary member. The negative pressure causes the flexible intermediary member to fold within the outer member to retract the retractable sheath. Next, the medical device is delivered at the treatment site.

In another embodiment, to deliver a device to a treatment site using an exemplary embodiment of the present invention, one carries out the following method. First, a medical device is advanced to a treatment site. The medical device is supported by an inner member and constrained by a retractable sheath during advancement. The retractable sheath is slideable over the inner member. The medical device, the inner member, and the retractable sheath are disposed within an outer member. A compressible member is connected to the retractable sheath and slidably disposed on the inner member. The compressible member is axially expandable. Next, the retractable sheath is retracted by axially expanding the compressible member. Next, the medical device is delivered at the treatment site.

In another embodiment, to deliver a device to a treatment site using an exemplary embodiment of the present invention, one carries out the following method. First, a medical device is advanced to a treatment site. The medical device is supported by an inner member and constrained by a retractable sheath during advancement. The retractable sheath is slideable over the inner member. The medical device, the inner member, and the retractable sheath are disposed within an outer member. A compressible member is connected to the retractable sheath and slidably disposed on the inner member. The compressible member is axially expandable. Next, the retractable sheath is retracted by axially compressing the compressible member. During advancement, the compressible member is filled with a fluid and to compress the compressible member, the fluid is withdrawn. Next, the medical device is delivered at the treatment site.

In another embodiment, to deliver a device to a treatment site using an exemplary embodiment of the present invention, one carries out the following method. First, a medical device is advanced to a treatment site. The medical device is supported by an inner member and constrained by a retractable sheath during advancement. The retractable sheath is slideable over the inner member. The medical device, the inner member, and the retractable sheath are disposed within an outer member. A compressible member is connected to the retractable sheath and slidably disposed on the inner member. The compressible member is axially expandable. Next, a constraint member is disposed on the outside of the compressible member. The constraint member limits a radial expansion of the compressible member. Next, the retractable sheath is retracted by axially expanding the compressible member with the constraint member radially limits the expansion of the compressible member. Next, the medical device is delivered at the treatment site.

In another embodiment, to deliver a device to a treatment site using an exemplary embodiment of the present invention, one carries out the following method. First, a medical device is advanced to a treatment site. The medical device is supported by an inner member and constrained by a retractable sheath during advancement. The retractable sheath is slideable over the inner member. The medical device, the inner member, and the retractable sheath are disposed within an outer member. A spring member is connected to retractable sheath and slidably disposed on the inner member, the spring member being axially expandable. The spring member is axially expandable. Next, the retractable sheath is retracted by axially expanding the spring member. Next, the medical device is delivered at the treatment site. In one embodiment, the spring member is locked in a compressed state during delivery and unlocked to allow the spring member to axially expand.

In any of the method described, the sheath retraction process can be controlled as previously described.

It is to be understood that even though numerous characteristics and advantages of various embodiments have been set forth in the foregoing description together with details of structures and function of the various embodiments, this disclosure is illustrative only. Changes may be made in detail, especially matters of structure and management of parts, without departing from the scope of the various embodiments.

The invention claimed is:

1. A catheter assembly comprising:
    an outer member;
    an inner member disposed within the outer member;
    a retractable sheath disposed over the inner member, the retractable sheath being slideable over the inner member; and
    a flexible intermediary member having a distal end directly attached to the retractable sheath and a proximal end attached to the outer member, the flexible intermediary member having a portion that is foldable within the outer member, wherein a seal is provided between the flexible intermediary member and the outer member; and
    wherein the flexible intermediary member is configured to retract or actuate the retractable sheath coupled thereto.

2. The catheter assembly of claim 1 wherein applying a negative pressure into said catheter assembly causes the portion that is foldable within the outer member to fold more into the outer member and to cause the retractable sheath to retract in a direction of the negative pressure.

3. The catheter assembly of claim 2 further comprising:
    a medical device supported by the inner member, wherein retracting the retractable sheath deploys the medical device.

4. The catheter assembly of claim 3 further comprising:
    a stopper disposed over the inner member and proximal to the medical device.

* * * * *